(12) United States Patent
Noguchi et al.

(10) Patent No.: US 7,426,027 B2
(45) Date of Patent: Sep. 16, 2008

(54) SMALL OBJECT IDENTIFYING DEVICE AND ITS IDENTIFYING METHOD

(75) Inventors: Masahisa Noguchi, Chiba (JP); Ken Tsukii, Tokyo (JP); Hideji Tajima, Chiba (JP)

(73) Assignees: Precision Systems Science Co., Ltd., Chiba (JP); The Furukawa Electric Co., Ltd., Tokyo (JP); Fi-Techno Co., Ltd., Chiba (JP)

( * ) Notice: Subject to any disclaimer, the term of this patent is extended or adjusted under 35 U.S.C. 154(b) by 0 days.

(21) Appl. No.: 11/867,585

(22) Filed: Oct. 4, 2007

(65) Prior Publication Data

US 2008/0037831 A1    Feb. 14, 2008

Related U.S. Application Data

(63) Continuation of application No. 10/470,208, filed as application No. PCT/JP02/00563 on Jan. 25, 2002, now Pat. No. 7,283,229.

(30) Foreign Application Priority Data

Jan. 25, 2001    (JP)    ............................. 2001-017630

(51) Int. Cl.
  *G01N 21/64*    (2006.01)
(52) U.S. Cl. ...................... 356/317; 356/417; 250/458.1
(58) Field of Classification Search ................... 356/72, 356/317, 318, 417; 250/458.1
  See application file for complete search history.

(56) References Cited

U.S. PATENT DOCUMENTS 4,184,766 A * 1/1980 Hogg ........................... 356/72

| | | | |
|---|---|---|---|
| 4,573,796 A | 3/1986 | Martin et al. | |
| 4,702,598 A | 10/1987 | Bohmer | |
| 5,760,900 A | 6/1998 | Ito et al. | |
| 5,824,269 A | 10/1998 | Kosaka et al. | |
| 6,592,822 B1 | 7/2003 | Chandler | |
| 2003/0142291 A1 | 7/2003 | Padmanabhan et al. | |
| 2004/0004043 A1 | 1/2004 | Terstappen et al. | |

FOREIGN PATENT DOCUMENTS

| JP | 03-110448 | 5/1991 |
| JP | 07-092077 | 4/1995 |
| JP | 07-325025 | 12/1995 |
| JP | 11-299477 | 11/1999 |

OTHER PUBLICATIONS

Bronwyn J. Batlersby et al., Toward Larger Chemical Libraries: Encoding with Fluorescent Colloids in Combinatorial Chemistry, J. Am. Chem Soc., 2000, pp. 2138-2139.

Japanese Patent Office, International Search Report, International Application No. PCT/JP02/00563, Feb. 19, 2002, 2 pages.

* cited by examiner

*Primary Examiner*—F. L Evans
(74) *Attorney, Agent, or Firm*—Haynes and Boone, LLP

(57) ABSTRACT

A small object identifying device and its identifying method according to which a large number of small objects can be identified. In one embodiment, the device includes a dispersion region section which disperses a large quantity of several kinds of small objects which are labeled by a combination of the presence/absence or measure of label elements of several kinds. A measuring device distributes and associates kinds of said label elements to two or more measurement points and measures the presence/absence or the measure of said label elements of the kinds which have been associated with respective measurement points. An identifying section associates the measurement results measured at each measurement point to thereby identify said small objects.

17 Claims, 18 Drawing Sheets

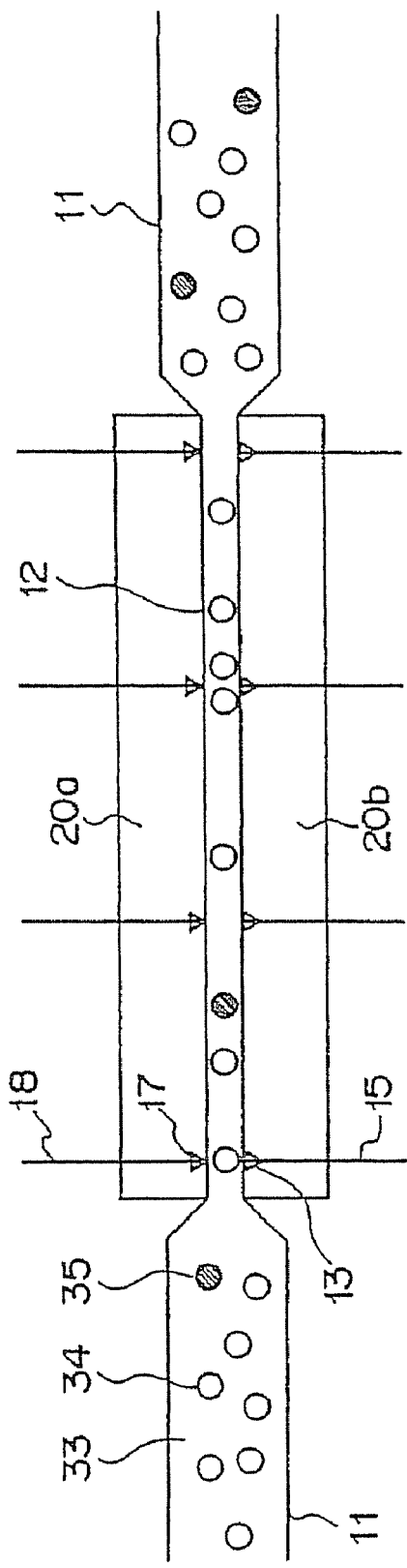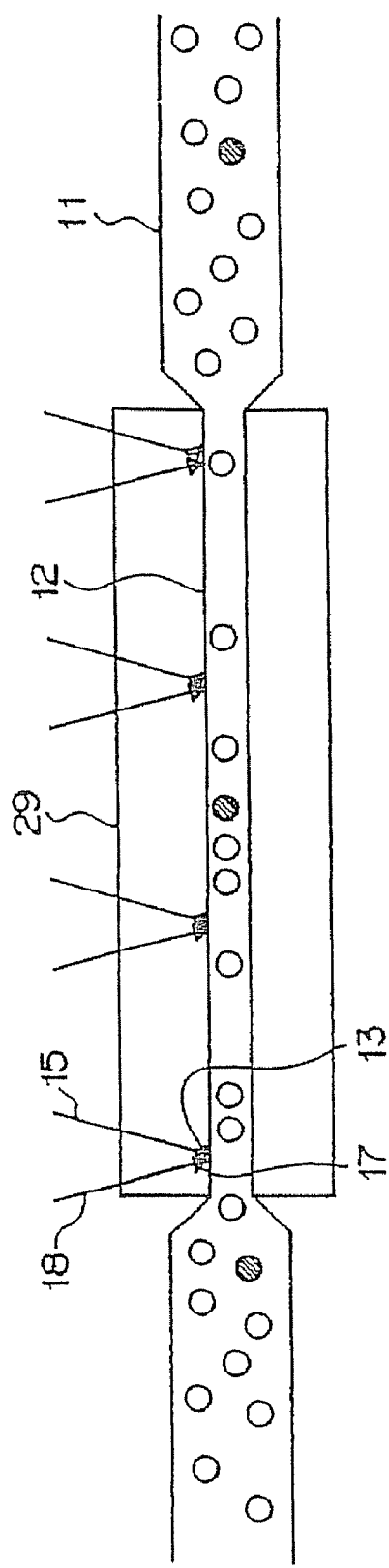
FIG. 2A
FIG. 2B

FIG. 3A
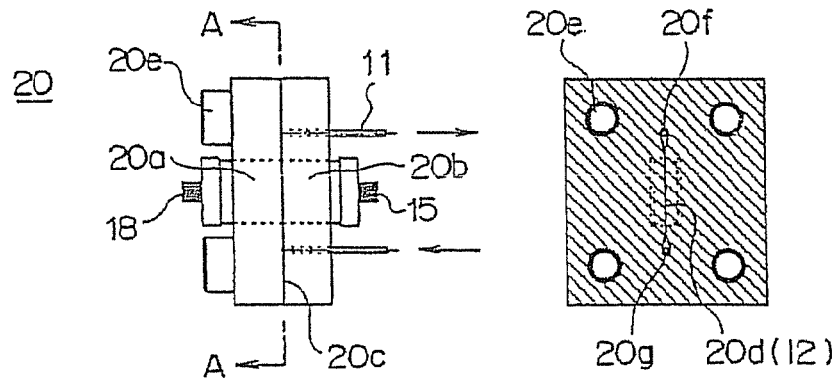
FIG. 3C
FIG. 3B
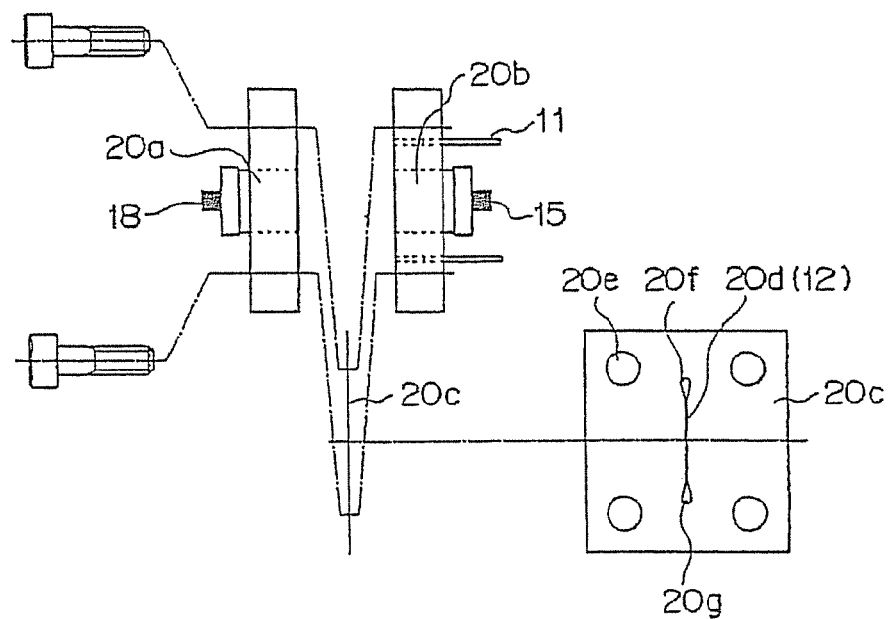
FIG. 3D
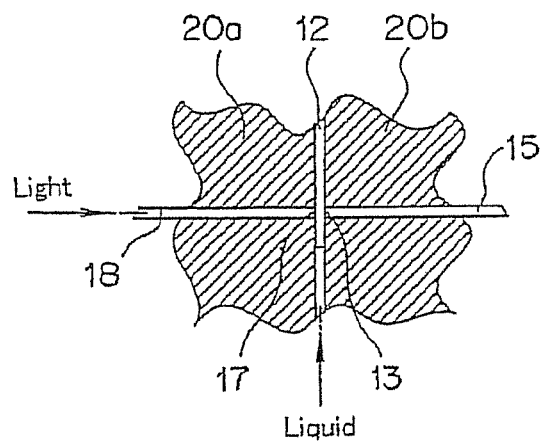

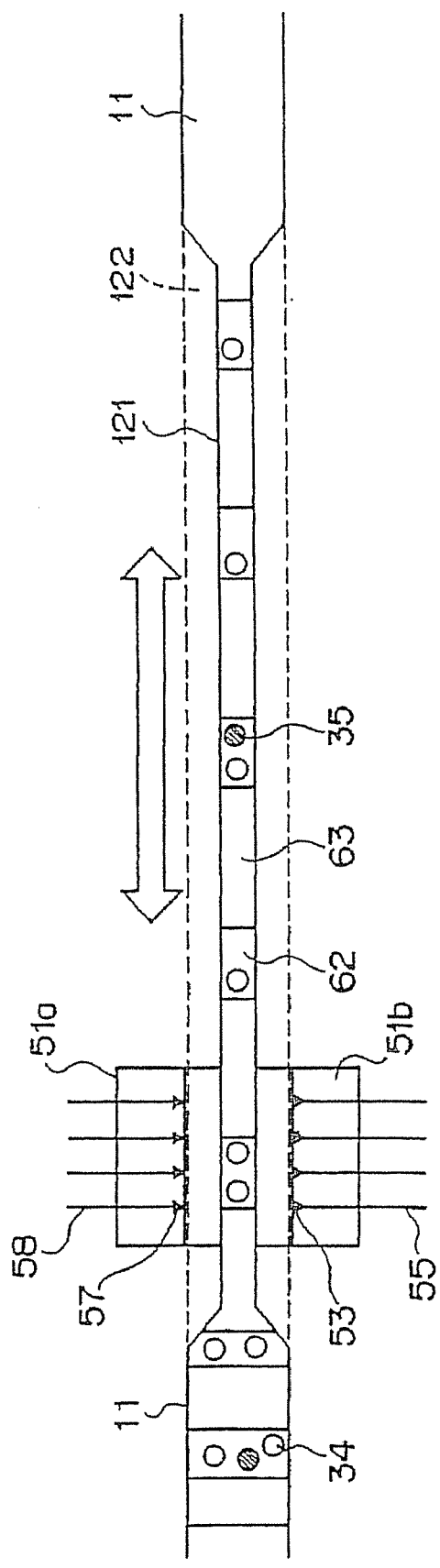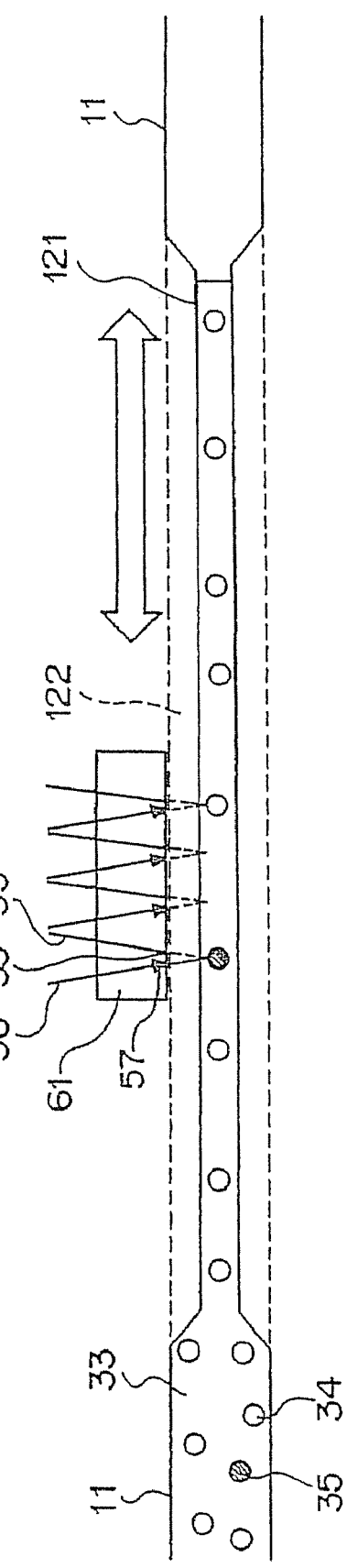

SMALL OBJECT IDENTIFYING DEVICE AND ITS IDENTIFYING METHOD

CROSS REFERENCE

This application is a continuation of U.S. patent application Ser. No. 10/470,208, filed Nov. 21, 2003, now U.S. Pat. No. 7,283,229, which is a national phase filing of international application no. PCT/JP02/00563, filed Jan. 25, 2002, which claims priority to Japanese patent application no. 2001-17630, filed Jan. 25, 2001, the disclosures of which are incorporated herein by reference.

TECHNICAL FIELD

The present invention relates to a small object identifying device and its identifying method. In particular, the present invention relates to all manner of fields, such as fields requiring inspections, analyses and diagnoses relating to genes, the immune system, proteins, amino acids, and biopolymer such as sugars, for example engineering fields, agricultural fields such as food, produce and seafood processing, pharmacology fields, medical fields such as sanitation, health, immunization, disease and genetics, and scientific fields such as chemistry or biology.

BACKGROUND ART

Heretofore, in identifying target small objects which are labeled with a fluorescent substance or the like, this is performed using a flow cytometer 160 such as shown in FIG. 18. The flow cytometer 160 has a passage 151 whereby a fluid containing the target small object flows along the interior. The passage 151 fluidicly couples a water flow tank 157 to a transport pump 158, which, in turn, is fluidicly coupled to a measuring passage 152 formed from a material with transmittance.

At a measuring position on the outside of the measuring passage 152 there is provided a light source 154 which shines excitation light of one type over a wide region on this measuring passage 152, and a light receiving section 153 which receives the fluorescence generated from fluorescent material which is provided on target small objects existing in the illumination region. The strength of the received light is analyzed by an analyzing section 155, to thereby detect the presence or absence of the target small objects. In the passage 151 there is provided in addition, the transport pump 158, diverter valves 159 and 161, and a waste tank 163. Reference symbol 156 denotes a suction mechanism, which is for drawing up the liquid containing the small objects to inside the passage 151 from a container 21 provided on the outside, via a nozzle 162.

Incidentally, conventionally there is a device for detecting the presence/absence of the target small objects which are labeled by the one type of labeling substance, and by using the flow cytometer, it is possible to measure the presence/absence thereof. However, recently, for the determination or analysis of base sequences of DNA, there is a growing requirement to label target substances of a large number of kinds.

In order to label target substances of a large number of kinds in this manner, it is not sufficient to merely use labeling substances of a plurality of different kinds for the small objects, and it is necessary to also specify the quantity ratio (molar ratio) in labeling (International Patent Publication WO 00/5357, Masayuki Machida et. al.). At this time, in order to obtain information from the labeling substances for each of the small objects, it is necessary to be able to independently measure the many small objects one at a time, so that information from the many kinds of labeled small objects is not measured overlapped.

Furthermore, in the case where several kinds of labeling substances are used, it is necessary to measure all of the various pieces of information obtained from the same small object.

However, if for the same small object, several kinds of excitation light are shone simultaneously all together, and the several kinds of light are received simultaneously all together without exception, since the plurality of light source sections and the plurality of light receiving sections are provided centralized, then in the measuring position, the construction of the optical measuring unit is centralized and complicated. Moreover, due to the influence of light shining from the various light source sections, there is the possibility that reception of the necessary light may be obstructed. Therefore, there is the problem that the number of kinds of labeling substance which one small object can have is naturally limited.

Moreover, with a device for small objects labeled by fluorescent substances of several kinds, which shines excitation light of several kinds onto a comparatively wide region at one measurement position of the passage, and receives the light of several kinds from the small objects which are in the comparatively wide region, there is a problem in that it is not possible to individually identify the small objects of several kinds which are labeled by the several kinds of labeling substances.

Therefore, the present invention addresses the aforementioned problems with a first object of providing a small object identifying device and its identifying method in which, by paying attention to the label elements which the respective small objects have rather than paying attention to each small object and measuring at once all of the label elements on the small object for each small object, and resolving for each of the label elements of a small number of kinds compared to the kinds of small objects, and providing a time difference and measuring, then the structure for the respective measurement points can be simplified as much as possible. Furthermore the amount of light to be shone can be reduced and the adverse affect on the received light can be reduced as much as possible, and the small objects can be identified, surely and with high reliability.

A second object is to provide a highly accurate small object identifying device and its identifying method which, by providing a time difference at two or more measurement points for a single small object and measuring, can measure the various different attitudes and directions between the measurement points for a single small object, and which can measure the label information from the respective small objects without exception.

A third object is to provide a highly accurate small object identifying device and its identifying method which, by dispersing a large quantity of small objects and providing a relative temporal relationship at two or more measurement points and then measuring, the influence of overlapping of the small objects can be eliminated as much as possible.

A fourth object is to provide a small object identifying device and its identifying method which can identify easily, reliably and efficiently a large number of small objects from several tens, to several hundreds, to several thousands, to more than several tens of thousands, without stopping in the case of identifying several kinds of small objects.

A fifth object is to provide a small object identifying device and its identifying method which is applicable to analysis, diagnosis and inspection of DNA, immune systems, proteins, amino acids, and biopolymers such as sugars.

A sixth object is to provide a small object identifying device and its identifying method with flexibility and diversity which can flexibly correspond according to the processing purpose.

DISCLOSURE OF THE INVENTION

In order to address the above mentioned technical problems, a first aspect of the invention is a small object identifying method comprising: a dispersion step for dispersing a large quantity of several kinds of small objects labeled by a combination of the presence/absence or measure of label elements of several kinds; a measuring step for distributing and associating kinds of the label elements to two or more measurement points, and measuring the presence/absence or the measure of the label elements of the kinds which have been associated with respective measurement points, for each of the dispersed small objects, at respective measurement points having a relative temporal relationship between measurement points; and an identifying step for associating the measurement results measured at each measurement point, based on the temporal relationship and a positional relationship between the measurement points to thereby identify the small objects.

Here "small object" refers to particulate objects such as, for example, particulate objects having a magnitude of the order of 0.1 μm to 100 μm. These may be formed from polystyrene, foam type material, magnetic material and the like. "Presence/absence or the measure of label elements" refers to the presence/absence or measure of elements which can be mutually identified such as, for example, for the small object itself and/or qualities thereof, or for the labeling substance on the small object and/or qualities of the labeling substance. As a result, the presence/absence or measure of elements includes the presence/absence or measure of qualities such as, for example, the measure of size, the material refractive index, reflectivity, magnetic susceptibility, electric field or magnetic field strength, or the wavelength of electromagnetic waves (radio waves, visible light, ultraviolet rays, infrared rays, X-rays etc.), the strength of electromagnetic waves and the like.

Here electromagnetic waves are not limited to the case where the small object itself or the labeling substance of the small object emits these, but also include the case of labeling by receiving the influence of electromagnetic waves from other than the small object or the labeling substance (for example by reflection, transmission, shading, absorption and the like).

"Measurement at respective measurement points having relative temporal relationships between respective measurement points" refers to measurement where the measurement time can be relatively specified at the respective measurement points. As a result, measurements at the respective measurement points can be performed by providing a time difference. Therefore, compared to the case of measurement at one time, the equipment configuration at the respective measurement points can be simplified.

Moreover, by measuring with a temporal relationship at two or more measurement points in relation to a single small object, the possibility of measuring information from a condition where occasionally multiple small objects are overlapped, is excluded. Furthermore, due to fluctuations of the small objects at the respective measurement points, or due to differences in the attitude, direction or form which the small objects have between the respective measurement points, the label information from the respective small objects can be measured without exception. The number of measurement points is determined based on the essence of the label element, the number of kinds of the label element, the processing purpose, the layout condition, the small object size and the like.

Regarding the "measurement points", by configuring these so as to occupy a predetermined small area determined by the magnitude of the small objects, the area occupied by the respective measurement points can be limited to a predetermined small area of a degree where at most one small object exists, so that for the respective measurement points, it is possible to avoid measuring with multiple small objects overlapped.

A second aspect of the invention is a small object identifying method according to the first aspect, wherein the dispersing step comprises an introducing step which disperses by introducing a liquid for suspending a large quantity of the several kinds of small objects to inside a predetermined dispersion region section, and the measuring step imparts a velocity along a predetermined movement direction, to the small objects or to two or more measurement points arranged along the movement direction on the surface of the dispersion region section or on the outside thereof, to thereby measure by making the temporal relationship relative between each of the measurement points.

Here "dispersion region section" refers to the region arranged so that the individual small objects can be measured in a separated condition, and so that the small objects are arranged without being scattered around with in this region. For example this is the passage or the container. "Passage" refers to a passage inside which a fluid can flow, "container" refers to an item for storing a liquid or the like inside. These are for example a structure such as; a tube, a groove, a gap, a recess, a flat surface and the like.

The passage portion provided with the measurement points need not necessarily be a small diameter, and may be a thin plane shape. Furthermore "small diameter" is not limited to the case of a straight line passage, and also includes the case where the passage is bent in a curve. Regarding the size of the "dispersion region section", an optimum or appropriate size is determined based on for example; the size of the small object, the characteristic of the liquid, the positional relationship, the temporal relationship, and the like. For example, the size of the "small diameter" may be for example twice the diameter of the small object.

"Predetermined movement direction" refers to the direction which the velocity imparts to the measurement points or to the small object. For example in the case where the dispersion region section is a small diameter passage, the longitudinal direction thereof is suitable.

"Velocity" can be imparted to either the small object, the measurement points, or to both of these. This velocity is determined for example by; the density, size, shape, or mass of the small object, the size, length, diameter or shape of the dispersion region section, characteristic such as the viscosity and specific gravity of the liquid, the purpose of the inspection or process, or the performance of the apparatus.

Moreover, in the "introducing step", in the case for example where the small objects contained in the liquid are labeled by a labeling substance which uses a substance requiring excitation light to emit light such as a fluorescent substance or a phosphorescent substance, as the label element, then the "measuring step" has at either one of the measurement points, an excitation step which irradiates an electromagnetic wave containing for example light having a wavelength which excites for example the fluorescent substance, or which exerts an electric field.

Moreover, in the "introducing step" in the case for example where the small objects contained in the liquid are labeled by colors of several kinds, then the "measuring step" preferably has for any one of the plurality of the measurement points, an illumination step which illuminates at least three kinds of visible light or the like having a spectrum of a wavelength range of a subtractive color mixture in which the three primary colors are each absorbed.

According to the first aspect of the invention, the small objects can be identified by a combination of the presence/absence or the measure of the label elements of several kinds, for example by a combination of strengths corresponding to the wavelength range of the several kinds of electromagnetic waves. Therefore it is possible to identify the small objects of many kinds, for example of the order of tens, hundreds, thousands, tens of thousands.

Moreover, in this aspect of the invention, in the case where attention is given to one small object, this has a relative temporal relationship and positional relationship at a plurality of measurement points, and each label element on this small object is measured. Consequently, for one small object, it is possible to measure various different attitudes, directions or forms, and the labeling information from each small object can be measured without exception. Hence identifying accuracy is high.

Furthermore, in this aspect of the invention, by dispersing many small objects, and providing a time difference as the relative temporal relationship at the measurement points being the two or more different positions, the influence of overlapping of the small objects can be excluded as much as possible, enabling measurement with high reliability.

Moreover, according to this aspect of the invention, the structure for the respective measurement points is simplified as much as possible. Furthermore, the small objects can be identified with reliability and high dependability, with a minimum amount of light for illumination, and the adverse affects on light reception reduced as much as possible.

Furthermore, according to the present invention, this can be applied to analysis, diagnosis and inspection of DNA, immune systems, proteins, amino acids, and biopolymers such as sugars. Moreover, depending on the purpose of the examination, various conditions can be set for the equipment and the like. Therefore identification of small objects with flexibility and diversity can be performed.

According to the second aspect of the invention, a small object identifying method may be provided wherein the measuring step measures by imparting a velocity to the introduced small objects, and then while these pass through the dispersion region section, electromagnetic waves are received at a plurality of fixed measurement points on the surface of the distribution region section or on the outside thereof, and the identifying step identifies kinds of the small objects by mutually associating the strength of the electromagnetic waves which are received for each of the measurement points, based on the velocity.

According to this aspect of the invention, it is possible to measure at the fixed measurement points. Therefore the mechanism for moving the measurement points can be omitted, and the construction thus simplified.

Furthermore, the velocity is imparted to the small objects, and when measuring at the fixed positions, rather than measuring in a condition where the small objects are stationary, the same small objects move so as to take various attitudes at each measurement point. Therefore, the labeling substance or the properties etc. for the small objects, can be reliably captured without exception. Furthermore, also between a plurality of small objects, since these move so as to take various attitudes at each measurement point, then for example even if these are overlapped at a certain measurement point, there will be a certain measurement point where they are separated, so that the possibility of independently measuring individual small objects is high.

Moreover, in the second aspect of the invention, this may be a small object identifying method wherein, the measuring step measures by receiving electromagnetic waves at a plurality of the measurement points which move at a predetermined movement velocity along the predetermined movement direction on the outside of the surface of the dispersion region section, in a condition with the small objects which have been introduced to the dispersion region section accumulated inside the dispersion region section, and the identifying step identifies kinds of the small objects by mutually associating the strength of the electromagnetic waves which are received for each of the measurement points, based on the predetermined movement velocity.

According to this aspect of the invention, the movement velocity of the measurement points can be controlled precisely mechanically. Hence the correspondence with the small objects can be performed reliably, and reliability is thus high.

Furthermore, in the second aspect of the invention, this may be a small object identifying method wherein, the measuring step measures the strength of the electromagnetic wave by receiving the electromagnetic waves at two or more of the measurement points which move at a predetermined movement velocity along the predetermined movement direction, while passing the small objects at a predetermined velocity through the dispersion region section, and the identifying step identifies the kind of the small objects by mutually associating the strength of the electromagnetic waves which are received for each of the measurement points, based on the predetermined velocity and the predetermined movement velocity.

According to the second aspect of the invention, by introducing the liquid suspending a large number of the small objects, to inside the dispersion region section, and imparting a predetermined velocity to the measurement points or the small object, the presence/absence or the measure of label elements which have a time difference between each other at two or more measurement points, can be measured with high reliability, simply and surely.

A third aspect of the invention is a small object identifying method wherein, in the measuring step, the two or more measurement points are arranged in one row or a plurality of rows along the predetermined movement direction, and the arrangement directions thereof are parallel with the predetermined movement direction, and the measurement direction for the measurement points belonging to the same the row are parallel with each other.

According to this aspect of the invention, the array direction of the measurement points and the predetermined movement direction are parallel, and also the measurement directions for the measurement points belonging to the same row are parallel with each other. Therefore this can be limited to small objects being the target measurement objects which are inside the dispersion region where planes which are extended so as to contain the measurement direction and the array direction intersect. Therefore intermixing of data, or errors (in size and strength etc.) are cancelled. Furthermore, since the respective measurement points are arranged in rows along the flow direction of the small objects, then mutual interference at the same time is avoided, and measurement accuracy and reliability is improved.

Furthermore, also for the illumination points, preferably the arrangement directions thereof and the predetermined movement directions are parallel, and the illumination directions for the illuminations points belonging to the same rows are parallel with each other. In this case, it is preferable that the respective flat planes which are extended so as to contain the array direction of the illumination points and the predetermined movement direction, and the respective flat planes related to the measurement points, intersect within the dispersion region section. As a result, high reliability measurement at a greater accuracy can be realized. Here "measurement direction" or "illumination direction" is the direction of reception (light) of electromagnetic waves of light or the like, or the direction of shining (illumination) of electromagnetic waves of light or the like, and for example coincides with the optical axis direction of the measurement points or the tip portions of the fibers being the illumination points. This optical axis is arranged for example so that this is perpendicular to the central axis of the dispersion region section.

A fourth aspect of the invention is a small object identifying method wherein the dispersion step involves surrounding a liquid containing the small objects having a velocity along the movement direction of the small objects, about a perpendicular direction to the velocity direction, with a liquid which does not contain small objects and which has a relative velocity with respect to the dispersion region section.

According to this aspect of the invention, the dispersion region section flows so that the liquid containing the small objects is a core flow and is surrounded by liquid which does not contain small objects. Such a core flow passes for example through a thin pipe, a channel, a gap, a concave shape passage or an injector, and is introduced to a passage or container which is thicker than the passage and which flows liquid not containing the small objects. At this time, the passage or injector which flows the liquid containing small objects, and the passage or container which flows the liquid not containing small objects preferably have a common axis. By making the downstream from this core flow introducing tip, so that the flow cross section is gradually reduced along the flow direction, the flow in the dispersion region section further downstream from the core flow introducing tip is stabilized, and for example the thinness and thickness of the passage and the flow velocity and the like can be adjusted so that the small objects pass through the measurement points one at a time. At this time, the thick passage or container preferably have a conical incline face which gives a gradual taper.

According to the fourth aspect, a stabilized flow of small objects can be obtained in the dispersion region section. Therefore measurement of the small objects at the measurement points can be reliably performed.

A fifth aspect of the invention is a small object identifying method wherein, in the first aspect, in the measuring step, the kinds of label elements are ones which emit electromagnetic waves of wavelengths of mutually different ranges, and the measure of label elements is the strength of the electromagnetic waves which the label elements emit, and the several kinds of labeled small objects are mutually identified by differences in combinations of wavelength ranges of the electromagnetic waves which the label elements on the small objects emit, or combinations of the wavelength range and intensity ratio thereof.

"The label elements of various kinds which emit electromagnetic waves of mutually different wavelength ranges" are label elements of for example a fluorescent substance which emit various kinds of fluorescence. "The strength of the magnetic waves which the label elements emit" is determined by the amount of the label element. When the amount is greater, the strength of the electromagnetic waves is higher.

The reason for "intensity ratio" is because, the construction is easier to provide determination of the molar ratio (mainly between the small object pairs) of the label element for each of the small objects, than to provide determination of the amount of label elements for each of the respective small objects.

That is to say, according to this aspect of the invention, the label elements of several kinds are label elements of for example a fluorescent substance, and include a predetermined molar ratio therebetween with respect to the small objects of one kind, and the small objects of various kinds can be mutually identified by making the kind and the molar ratio of the label elements different.

Furthermore, "electromagnetic waves" includes not only visible light, but also radio waves of various wavelengths, infrared rays, ultraviolet rays, X-rays and the like. In the case of visible light and the like, this is transmitted by a predetermined fiber, and in the case of radio waves, a waveguide is used.

According to this aspect of the invention, regarding the small objects, in the respective measurement points, the presence/absence and measure of strength of electromagnetic waves thereof is measured for each of the wavelength ranges. Furthermore, any of the measurement points in the measuring step may be able to receive electromagnetic waves from the label elements of several kinds at one time, and measure the presence/absence and the measure thereof. In this case, the molar ratio between respective labeling substances can be measured certainly and with high reliability.

According to the fifth aspect of the invention, in the measuring step, the label elements of various kinds are ones which emit electromagnetic waves of wavelengths within mutually different ranges, and the measure of label elements is the strength of their electromagnetic waves, and the small objects which are labeled with several kinds are identified from each other by the combination of wavelengths of electromagnetic waves which the label elements on the small objects emit, or by differences in the combination of the wavelength and the intensity ratio thereof. According to this aspect of the invention, the small objects of many kinds can be positively identified with a simple device and easy analysis.

A sixth aspect of the invention is a small object identifying method wherein, the dispersion step disperses as the small objects, a reference small object having a label which becomes a distinct reference, together with the target small object, and the identifying step incorporates the measurement results for the reference small object, to thereby identify the kind of the target small object.

According to the sixth aspect of the invention, a liquid in which the reference small object which becomes the reference for the label, is suspended together with the target small object is introduced as the small objects, and the identifying step incorporates the measurement result of this reference small object. As a result, deviation in the measurement can be adjusted on the basis of the respective measurement points, the different times, and the different conditions, and highly accurate and highly reliable identification of the target small objects can be performed.

A seventh aspect of the invention is a small object identifying method wherein in the measuring step, in the case where the small objects are ones having a magnetic particle, measurement is performed by remotely controlling the dispersed small objects by applying or removing a magnetic field to or from the small objects.

In this case, the magnetic field may be exerted on the passage portion along a curve. As a result, this gives a state where the small objects are lined up in the flow direction, so that the small objects can be easily measured individually.

According to the seventh aspect of the invention, by applying or removing the magnetic field on or from the small objects, the target small objects can be accumulated inside the dispersion region, and are lined up, and the relative velocity between the measurement points can be freely controlled. Therefore positive measurement can be performed with accuracy.

An eighth aspect of the invention is a small object identifying method wherein, in the measuring step, in the case where the label element is a luminescent material which requires excitation light to emit light, the emission intensity thereof and the excitation light intensity which simultaneously excites the luminescent material are measured, and in the identifying step, the measurement value of the emission intensity is corrected based on the measurement value for the strength of excitation light which is simultaneously obtained, to thereby identify the small object.

Here, "label element is a luminescent material which requires excitation light to emit light" is for example a fluorescent substance or a phosphorescent substance. The strength of the excitation light is for example the transmitted light, the scattered light or the reflected light corresponding to the position where the excitation light is shone. According to this aspect of the invention, by correcting fluctuations in the transit positions of the small objects inside the dispersion region section, and deviations in the measurement values due to the fluctuations in the excitation light strength, measurement values of high reliability can be obtained.

According to the eighth aspect of the invention, by correcting deviations in the transit positions of the small objects inside the dispersion region section, and deviations in the measurement values due to the fluctuations in the excitation light strength, measurement values of high reliability can be obtained.

A ninth aspect of the present invention is a small object identifying device comprising: a dispersion region section which disperses a large quantity of several kinds of small objects which are labeled by a combination of the presence/absence or measure of label elements of several kinds; a measuring device which distributes and associates kinds of the label elements to two or more measurement points and measures the presence/absence or the measure of the label elements of the kinds which have been associated with respective measurement points, for the small objects which are dispersed inside the dispersion region section, at respective measurement points having a relative temporal relationship between measurement points; and an identifying section which associates the measurement results measured at each measurement point, based on the temporal relationship and a positional relationship between the measurement points, to thereby identify the small objects.

Furthermore, for a liquid in which a reference small object having a label which becomes a clear reference, is suspended together with the target small object, the identifying section may identify the kind of the target small object, by incorporating the measurement results for the reference small object.

Moreover, according to the ninth aspect of the invention, effects that are the same as those described for the first aspect of the invention are demonstrated.

A tenth aspect of the invention is a small object identifying device, wherein the measurement points of the measurement device are arranged along a predetermined movement direction on the surface of the dispersion region section or on the outside thereof, and there is provided a moving section which imparts a predetermined velocity along the predetermined movement direction to the measurement points or to the small objects.

Furthermore, in the tenth aspect of the invention, the movement section may be a fluid mechanism which moves so as to pass the small objects through the dispersion region section at a predetermined velocity. In this case, the identifying section may be one which identifies the kind of the small objects by mutually associating the measurement results obtained for each of the measurement points, based on the predetermined velocity.

Moreover, in the tenth aspect of the invention, the moving section may be one which has; an accumulation device capable of accumulating small objects inside the dispersion region section, and a moving body which moves a plurality of the measurement points at a predetermined movement velocity along a predetermined movement direction, on the outside of the surface of the dispersion region section. In this case, the identifying section is one which identifies kinds of the small objects by mutually associating the measurement results obtained for each of the measurement points, based on the predetermined movement velocity.

Furthermore, the moving section may be one which comprises; a fluid mechanism which moves the small objects so as to pass through the dispersion region section at a predetermined velocity, an accumulation device capable of accumulating small objects inside the dispersion region section, and a moving body which moves a plurality of the measurement points at a predetermined movement velocity along the predetermined movement direction on the outside of the surface of the dispersion region section. In this case, the identifying section may be one which identifies the kind of small objects by mutually associating the measurement results obtained for each of the measurement points, based on the predetermined velocity and the predetermined movement velocity.

According to the tenth aspect of the invention, effects that are the same as those described in the second aspect of the invention are demonstrated.

An eleventh aspect of the invention is a small object identify device wherein the two or more measurement points of the measurement device are arranged in one row or a plurality of rows along the predetermined movement direction, and the arrangement directions thereof are parallel with the predetermined movement direction, and the measurement direction for the measurement points belonging to the same row are parallel with each other. Furthermore, also for the illumination points, preferably the arrangement directions thereof and the predetermined movement directions are parallel, and the illumination direction for the measurement points belonging to the same rows are parallel with each other. According to the eleventh embodiment of the invention, effects similar to those described for the third aspect of the invention are demonstrated.

A twelfth aspect of the invention is a small object identifying device wherein within the dispersion region, a liquid containing the small objects having a velocity along the movement direction of the small objects with respect to the measurement points, is surrounded about a perpendicular direction to the velocity direction with a liquid which does not contain small objects and which has a relative velocity with respect to the dispersion region section.

According to the twelfth aspect of the invention, effects similar to those described for the third aspect of the invention are demonstrated.

A thirteenth aspect of the invention is a small object identifying device wherein the label elements are labeled so as to be mutually identifiable by differences in combinations of wavelength range of electromagnetic waves used in labeling the label elements, or combinations of their wavelength range and intensity ratio, and the measuring unit has; a plurality of wave receiving sections which receive electromagnetic waves at several of the measurement points being the surface of the dispersion region section or the outside thereof, an attachment jig which fixedly attaches the tips of the wave receiving section to the measurement points, and a measuring section which measures the intensity of the received electromagnetic waves for each of the wave receiving sections.

In the case where the measurement points are fixedly arranged in a predetermined movement direction on the surface of the dispersion region section or the outside thereof, the wave receiving sections also are fixedly attached to the surface of the dispersion region section or the outside thereof.

In the case where the moving section is a moving body which moves the plurality of measurement points at a predetermined movement velocity along a predetermined movement direction on the outside of the surface of the dispersion region section, the wave receiving section is attached to the moving body, and the attachment jig is one which fixedly attaches the wave receiving section to the moving body.

Furthermore, in the tenth aspect of the invention, the moving section comprises; a fluid mechanism which moves the small object at a predetermined velocity in the dispersion region section, an accumulation device capable of accumulating small objects inside the dispersion region section, and a moving body which mounts and moves a plurality of the wave receiving sections at a predetermined movement velocity along a predetermined movement direction on the outside of the surface of the dispersion region section, and the attachment jig may be one which fixedly attaches the wave receiving section to the moving body.

Here the measuring unit converts the strength of the electromagnetic waves received at the measurement points, into electrical signals based on the position of the measurement point, the velocity of the small objects or the measurement points, and a predetermined threshold value, and the identifying section may have a discriminating circuit which discriminates the kind of small object based on these electrical signals.

Furthermore, at this time, the measurement unit comprises for example; a photoelectric converting section which converts the strength of the light received by the measurement points into analog electrical signals, and an AD conversion section which converts the converted analog electrical signals into predetermined electrical signals synchronized with a time interval determined based on a predetermined velocity of the small objects or measurement points, corresponding to a threshold value of one or two or more voltages previously determined for each of the measurement points, and the identifying section may have a discrimination circuit which discriminates the kind of small objects based on the digital electrical signal at the measurement points.

According to the thirteenth aspect of the invention, the label elements are mutually labeled using electromagnetic waves, and the tips of the wave receiving sections which receive these electromagnetic waves are fixedly attached to the measurement points by the attachment jig. Therefore the mutual positional relationship of the measurement points is determined, and highly accurate identification can be performed.

A fourteenth aspect of the invention is a small object identifying device, wherein the identifying section, in the case where a reference small object having a label which becomes a distinct reference is dispersed together with the target small objects as the small object, incorporates the measurement result for the reference small object, to thereby identify the kind of the target small object.

According to this aspect of the invention, the same effects as for the sixth aspect of the invention are demonstrated.

A fifteenth aspect of the invention is a small object identifying device, wherein the measuring unit is an optical measuring unit, and the wave receiving section is a wave receiving section having a plurality of light receiving fibers which receive light from inside a dispersion region section with one or two or more tip portions provided at a plurality of measurement points along a predetermined movement direction on the surface of the dispersion region section or the outside thereof, and the attachment jig fixedly attaches the tip portions of the light receiving fibers of the optical measuring unit to the surface of the dispersion region section or the outside thereof, or a moving body capable of moving along the predetermined movement direction outside of the dispersion region section. The tips of the light receiving fibers preferably have an area corresponding to the predetermined small area.

In the fifteenth aspect of the invention, the optical measuring unit may be one where at the measurement points, light can be shone through the light receiving fiber to inside the dispersion region section. According to this aspect of the invention, the structure can be simplified.

Furthermore, according to this aspect of the invention, the dispersion region section may be for example a pipe with translucent properties and through which liquid can pass, and a protective material with translucent properties may be integrally provided on this pipe. In this case, since the dispersion region section is a pipe with translucent properties and integrally provided with the protective material with translucent properties, a moving body which moves the measurement point can be easily provided on the outside of the pipe.

In the fifteenth aspect of the invention, the measuring unit is an optical measuring unit, and a light receiving fiber is used as the wave receiving section or an illumination fiber is used as the illumination section.

Consequently, the positions of the individual small objects which are inside the dispersion region section can be accurately determined at pin points. Furthermore, the construction of the device overall can be made compact. Moreover, a strong light is not necessary for the light source, and it is not necessary to move the light source itself. Therefore the mechanism can be simplified, and the necessary energy can be reduced.

A sixteenth aspect of the invention is a small object identifying device, wherein the optical measuring unit has a plurality of illumination fibers with one or two or more tip portions provided at illumination points corresponding to the two or more measurement points, and the attachment jig attaches the light receiving fibers and illumination fibers to the diffusion region section so that the optical axes of the tip portions of the illumination fibers provided at the illumination points and the tip portions of the light receiving fibers provided at the measurement points coincide within a predetermined error range determined by the size of the small object, or intersect at a predetermined angle within the dispersion region section.

Here "the illumination fibers", in the case where the labeling substance on the small object is for example a fluorescent substance, then these are for exciting this, while in the case where the small object is labeled with colors of several kinds, then these each shine at least three kinds of visible light having spectrums of wavelength ranges which are each absorbed by the three primary colors of a subtractive color mixture, on any one of the plurality of the illumination points.

Furthermore, with regards to making "the optical axes of the tip portions of the illumination fibers provided at the illumination points and the tip portions of the light receiving fibers provided at the measurement points coincide within a predetermined error range determined by the size of the small object, or intersect at a predetermined angle within the dispersion region section", since the peak time point of the fluorescent intensity is close to the illumination time point of the excitation light, then this is so that a deviation does not occur in the times between the illumination time point and the light receiving time point, and so that the fluorescent intensity and the shading of the illumination light due to the small object can be measured simultaneously.

In the sixteenth aspect of the invention, in the case where the small objects are labeled with light emitting substances of several kinds which are excited by common excitation light or an electric field, the optical measuring unit, by shining the excitation light for any one of two or more of the measurement points, may receive light from the light emitting substances of several kinds at one time.

According to the sixteenth aspect of the invention, an effect similar to that described for the fifteenth aspect of the invention is demonstrated for luminescent materials which require excitation light.

A seventeenth aspect of the invention is a small object identifying device, wherein the attachment jig has; an illumination side holding section which holds the tip portions of the plurality of illumination fibers in an array such that their tip faces are positioned on an end face of the illumination side holding section or pass through the end face, and a light receiving side holding section which holds the tip portions of the plurality of light receiving fibers in an array such that their tip faces are positioned on an end face of the light receiving side holding section or pass through the end face, and so that a dispersion region section is formed between the two end faces of the illumination side holding section and the light receiving side holding section, the illumination side holding section and the light receiving side holding section are secured to the dispersion region section, and the dispersion region section is a long thin slit shape hole provided in a thin plate which is sandwiched from the front and rear by the two end faces of the illumination side holding section and the light receiving side holding section.

Here the light receiving side holding section and illumination side holding section may use for example the two terminals of an optical fiber connector, and the dispersion region section may be formed by providing a gap between the two terminals. Furthermore, the illumination side holding section and the light receiving side holding section may be formed for example from a resin member or a metallic member or the like, and may ones which hold each of the tip portions of the illumination fibers and the tip portions of the light receiving side fibers by embedding.

According to the seventeenth aspect of the invention, a similar effect to that described for the fifteenth aspect of the invention is demonstrated for the luminescent material which requires excitation light.

Furthermore, according to the seventeenth aspect of the invention, since the dispersion region section is a long thin slit shape hole provided in a thin plate which is sandwiched from the front and rear by the two end faces of the illumination side holding section and the light receiving side holding section, then this is easily manufactured with a simple construction.

An eighteenth aspect of the invention is a small object identifying device, wherein on the outside of the dispersion region section there is provided a magnetic force device which can remotely control the small objects by applying or removing a magnetic field to or from the inside of the region section.

Here in the case where the dispersion region section is a small diameter passage, at a portion of the measuring passage may be formed by bending in a predetermined curve, and the magnetic force device may be moveably provided so that the magnetic poles can be made to approach and separate from the measurement passage. The movement direction of the magnetic poles is preferably such that the magnetic field direction thereof is in the direction of the passage on the upstream side of the measurement passage. As a result, in the case where the small objects are magnetic particles, then by controlling the magnetic force device, the magnetic particles can be made to pass along the measurement passage in a lined up condition.

According to the eighteenth aspect of the invention, a similar effect to that described for the seventh aspect of the invention is demonstrated.

A nineteenth aspect of the invention is a small object identifying device, wherein in the case where the label elements are luminescent materials which require excitation light to emit light, the measuring unit is an optical measuring unit, and the optical measuring unit has; an illumination section which shines excitation light which excites the luminescent material in the illumination points corresponding to two or more of the measurement points, and a light receiving section which receives the excited luminescence and the excitation light in the measurement points, and the identifying section corrects the measurement value of the emission intensity based on the measurement value of the excitation light strength obtained at the same time, to thereby identify the small object.

According to the nineteenth aspect of the invention, a similar affect to that described for the eighth aspect of the invention is demonstrated.

A twentieth aspect of the invention is a small object identifying device, wherein the measuring unit is an optical measuring unit, and has a light receiving section having a plurality of light receiving fibers with one or two or more tip portions provided on a plurality of measurement point along a predetermined movement direction on the face or the outside of the dispersion region section, which receive light from inside the dispersion region section, and a plurality of illumination fibers with one or two or more tip portions provided at illumination points corresponding to two or more of the measurement points, and the core diameter of the tip portions of the light receiving fibers is smaller than the core diameter of the illumination fibers.

Here the core diameter of the tip portions of the light receiving fibers is preferably for example approximately 50 to 65% of the core diameter of the illumination fibers.

According to the twentieth aspect of the invention, the measurement sensitivity can be improved with respect to deviations of the positions through which the small objects pass inside the dispersion region section.

BRIEF DESCRIPTION OF THE DRAWINGS

FIGS. 2A and 2B are enlarged views in the vicinity of a measurement passage of the small object identifying device according to the first embodiment of the present invention.

FIGS. 3A, 3B, 3C and 3D are detailed views of an attachment section according to a first embodiment of the present invention.

FIGS. 8A and 8B are enlarged views of a measuring passage of the small object identifying device according to the second embodiment of the present invention.

BEST MODE FOR CARRYING OUT THE INVENTION

A small object identifying device and its identifying method according to embodiments of the present invention is described based on the drawings. The description of these embodiments is not to be interpreted as limiting to the present invention, except as particularly specified.

Figure 1:
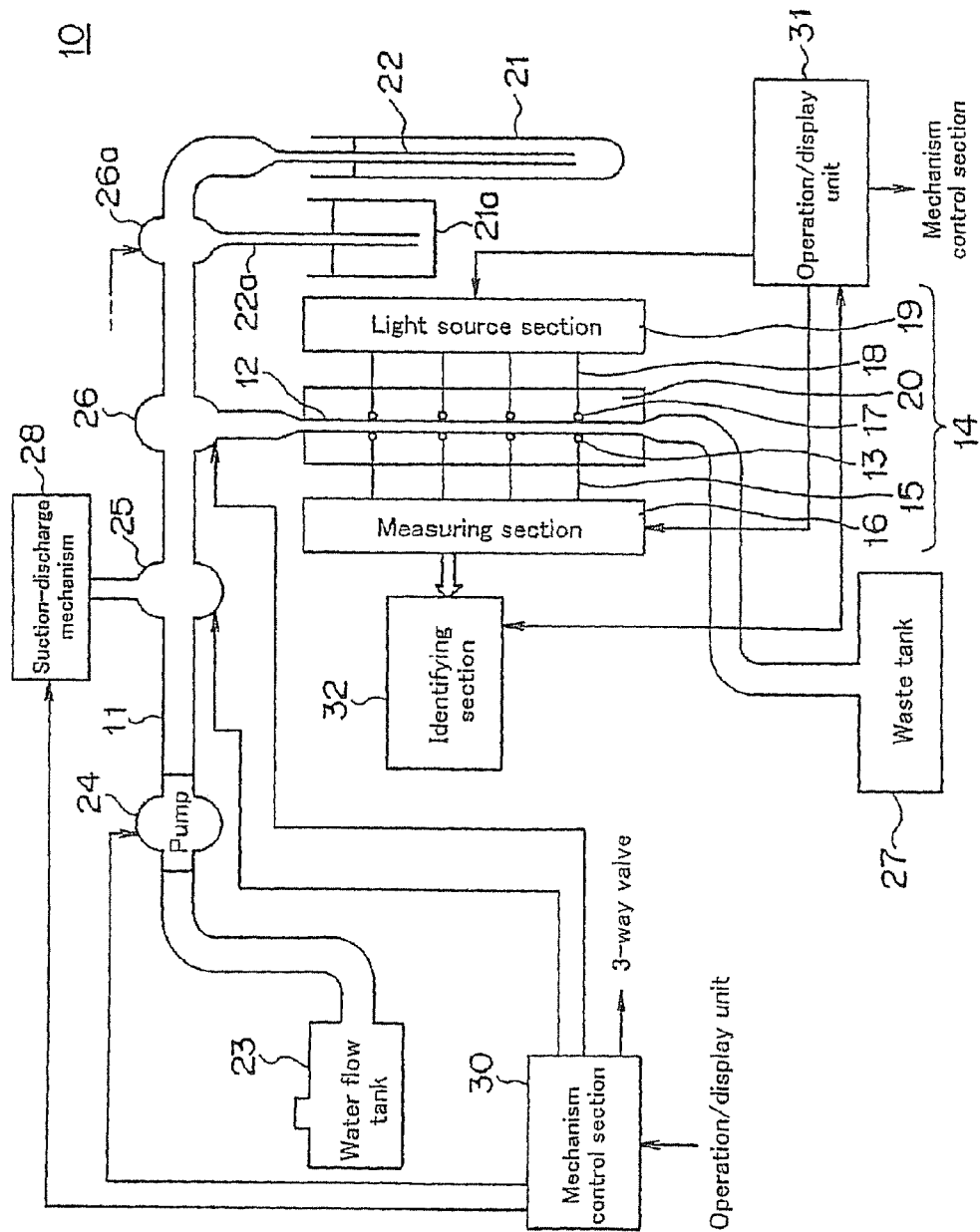
FIG. 1 is an overall conceptual diagram of a small object identifying device according to a first embodiment of the present invention.
Figure 4A:
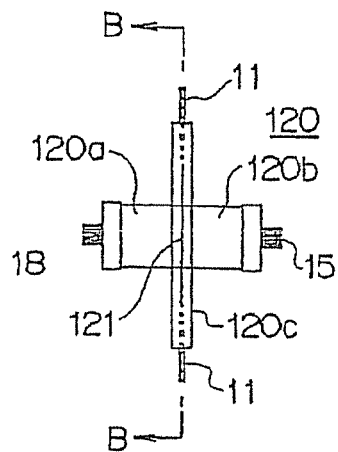
FIGS. 4A, 4B, 4C and 4D are detailed views of another example of an attachment section according the first embodiment of the present invention
Figure 4C:
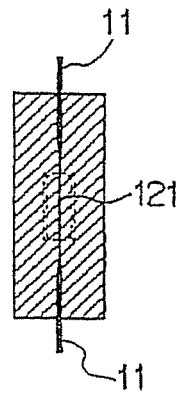
Figure 4B:
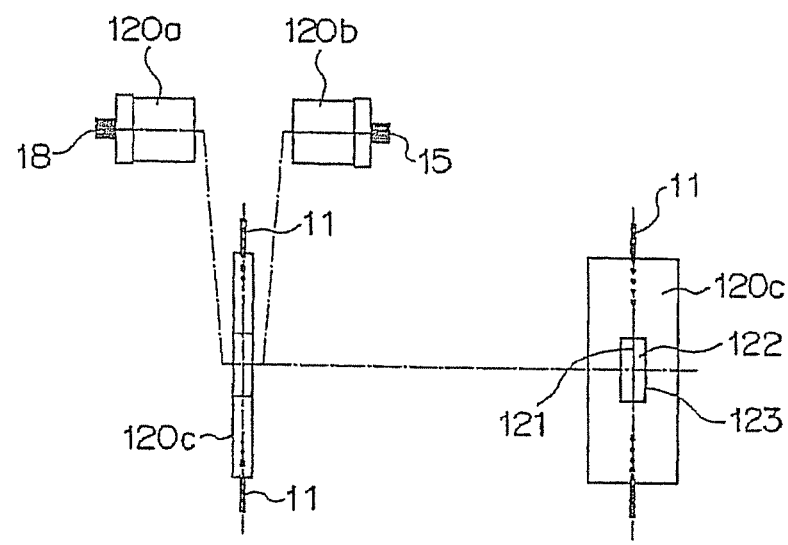
Figure 4D:
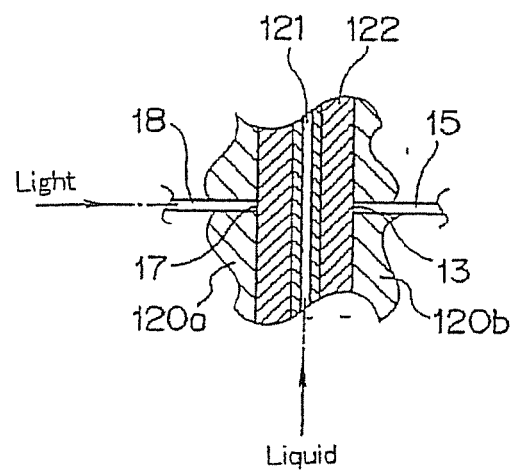
Figure 5B:
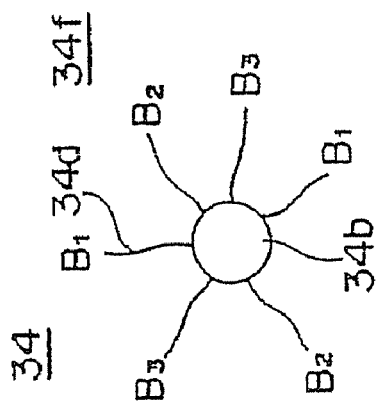
FIGS. 5A, 5B, 5C, 5D and 5E are views showing an example of a small object according to the first embodiment of the present invention.
Figure 5C:
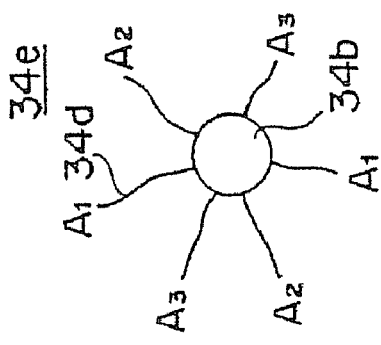
Figure 5A:
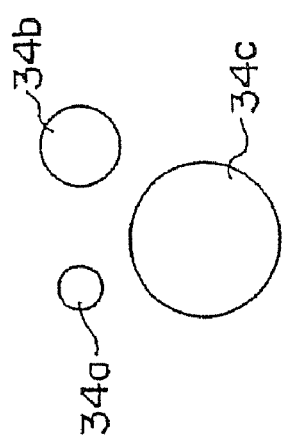
Figure 5D:
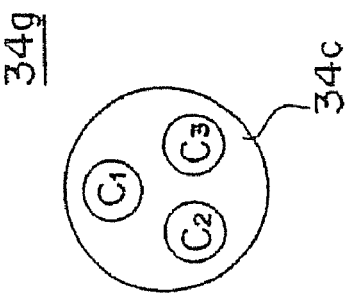
Figure 5E:
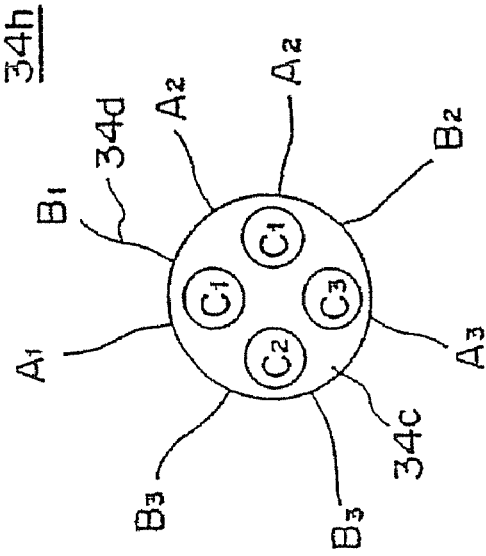

FIG. 1 shows the whole of a small object identifying device 10 according to a first embodiment. This small object identifying device 10 has a small diameter passage 11 serving as a dispersion region section inside which flows a liquid containing a large quantity of target small objects of several kinds which are labeled by a combination of the presence/absence or the measure of label elements of several kinds A part of this passage 11 is a measuring passage 12 for performing measurement of the small objects contained in the liquid. On the surface of the measuring passage 12 fixedly provided at predetermined positions along the passage direction, is provided a row of two or more (in this example four are shown to simplify explanation) measurement points 13 on a straight line, for performing measurement of the distributed kinds of the label elements, having a relative temporal relationship.

This small object identifying device 10 has an optical measuring unit 14 which measures the strength of the electromagnetic waves proceeding from the liquid introduced to the passage 11 and in the side face direction of the passage 11, as the label element, and measures the temporal fluctuations in the strength of the electromagnetic waves of a wavelength range which is associated with each measurement point 13, by providing a predetermined time difference for the respective measurement points 13. The measurement points 13 are spatially distributed along the direction of the passage 11.

This optical measuring unit 14 has light receiving fibers 15 serving as multiple light receiving sections, with tip ends provided on the measurement points 13, and a measuring section 16 for measuring the strength of received light for the wavelength range which is associated with each of the light receiving fibers 15. The optical axis direction of the tip end portions of the light receiving fibers 15 are mutually parallel, and in this example, are perpendicular to the passage direction, and are directed towards the central axis of the passage 11. The small areas of the tip ends of the fibers 15 are set to a size and position so as to include the whole of one small object, but so as to not include two or more small objects.

Furthermore, the optical measuring unit 14 has a plurality of illuminating points 17 which can shine a light, so that in the case where a fluorescent substance on the small object is adopted as the label element, this is excited and the fluorescent intensity is measured to thereby identify the small object, and in the case where the magnitude of the small object is adopted as the label element, the strength of the illuminating light which is shut off by the small object is measured to thereby identify the size of the small object. The plurality of illumination points 17 are provided in a row on a straight line along the passage direction, corresponding to the respective measurement points 13 on the side face of the measuring passage 12.

Furthermore, the optical measuring unit 14 has illumination fibers 18 serving as the illumination section, with the tips provided so as to be able to shine excitation light at the plurality of illumination points 17, and a light source section 19 such as a laser source, a xenon lamp, or a xenon-mercury lamp or the like for supplying excitation light to the illumination fibers 18. The illumination direction of the tip end portions of the illumination fibers 18 are mutually parallel, and in this example, are perpendicular to the passage direction, and are directed towards the central axis of the passage 11. Regarding the small areas of the tip ends of the fibers 18, these are set to a size so as to include the whole of one small object, but so as to not include two or more small objects.

The illumination points 17 and the measurement points 13 are provided so as to face each other with the measuring passage 12 therebetween, and are fixedly attached to the measuring passage 12 by means of an attachment jig 20, so that the optical axes of the respective tip portions of the light receiving fibers 15 and the illumination fibers 18 coincide within an error range determined by the size of the small objects.

The passage 11 of this small object identifying device 10 comprises in sequence; a water flow tank 23 which contains a liquid such as water for diluting the liquid which suspends the target small objects, a transport pump 24 for transporting the liquid inside the passage 11, three-way valves 25, 26 and 26a for switching to connect two passages selected from the three passages, the measuring passage 12, and a waste tank 27 which contains liquid to be disposed.

Furthermore, there is provided; a suction nozzle 22 provided on the outer portion of the passage 11, which can be inserted into the container 21 storing the liquid containing the small objects, and which can draw up a liquid from the container 21, a washing nozzle 22a also provided on the outer portion of the passage 11, which can draw up a cleaning solution from a container 21a storing a cleaning solution, and a suction-discharge mechanism 28.

The inner diameter and length of the passage 11 or the measuring passage 12 and the physical quantities such as the flow velocity of the liquid flowing thereinside are determined by for example; the diameter of the small objects being used, the diameter of the passage, the labeling substance being used, the density, the specific gravity of the liquid being used, the viscosity, or the purpose of use. Furthermore, in the small object identifying device 10 according to the present embodiment, there is provided a mechanism control section 30 for controlling the mechanism for the three-way valves 25, 26 and 26a, the suction-discharge mechanism 28, and the transport pump 24.

Here, the transport pump 24 corresponds to the moving section for moving the small objects at a predetermined velocity. Moreover, there is provided an operation/display unit 31 which executes operation and instructions for the optical measuring unit 14 and the mechanism control section 30, and which is provided with a display section and information processing section (not shown in the figure).

Reference symbol 32 denotes an identifying section which identifies the kind of small object, by mutually relating the strength of the obtained electromagnetic waves based on the velocity of the small objects inside the measuring passage 12, at predetermined time differences for each of the respective measurement points 13 of the optical measuring unit 14.

FIG. 2 (a) shows an enlarged outline of the measuring passage 12 portion shown in FIG. 1. A high density suspension suspending the target small objects which is introduced to the passage 11 is mixed with water from the water flow tank 23, and the diluted liquid 33 is controlled so as to pass through within the measuring passage 12.

Moreover, in this liquid 33 is suspended reference small objects 35 having a characteristic of shape, size, refractive index, reflectivity, emission wavelength, emission intensity or the like, which perform labeling of a predetermined definite reference or which becomes a predetermined definite reference. The identifying section 32, based on measurement results for the target small objects 34 and the reference small objects 35, identifies the kind of the several kinds of small objects. As a result, the unification and adjustment of measurement results in the case of using different samples, or different apparatus such as measuring equipment, passages etc., is possible, and also prevention of errors in the measurement results is possible.

Here, reference symbol 20a denotes an illumination side holding section. This holds the tip portions of the plurality of illumination fibers 18 arranged for example in a row so that the tip end faces of the illumination fibers 18 are positioned on the respective illumination points 17 at their end faces. Reference symbol 20b is a light receiving side holding section. This holds the tip portions of the plurality of light receiving fibers 15 arranged for example in a row so that the tip end faces of the light receiving fibers 15 are positioned on the respective measurement points 13 at their end faces.

The measuring passage 12 is formed between the end face of the light receiving side holding section 20b and the end face of the illumination side holding section 20a. At this time, as shown in FIG. 2 (a), the optical axes of the light receiving side holding section 20b and the tip end portions of the fibers 15 and 18 of the illumination side holding section 20a are provided so as to coincide. The illumination side holding section 20a and the light receiving side holding section 20b form respective terminals for the optical fiber connector.

FIG. 2 (b) shows another example of an optical measuring unit according to the first embodiment. In this example, the measurement points 13, the illumination points 17 and the light receiving fibers 15, and the illumination fibers 18 are provided so that the optical axes of the tip portions of the light receiving fibers 15 and the optical axes of the tip portions of the illumination fibers 18 intercept at a predetermined angle within the measuring passage 12. Reference symbol 29 denotes an attachment jig for attaching the light receiving fibers 15 and the illumination fibers 18 to the measuring passage 12.

FIG. 3 shows the attachment jig 20 in more detail. The attachment jig 20 according to this embodiment as shown in FIG. 3 (a) comprises; an illumination side holding section 20a in which is provided the illumination fibers 18, a light receiving side holding section 20b in which is provided the light receiving fibers 15, and a thin plate 20c made for example of metal foil provided between the end faces of the two holding sections 20a and 20b. Reference symbol 20e denotes screws for fixedly attaching the illumination side holding section 20a, the light receiving side holding section 20b and the thin plate 20c. Furthermore, the passage 11 passes through the light receiving side holding section 20b up to the thin plate 20c, so as to be perpendicular to the face of the thin plate 20c.

FIG. 3 (b) is an exploded view showing the attachment jig 20 shown in FIG. 3 (a) disassembled. In the approximate center of the thin plate 20c is provided a rectangular hole 20d of a slit shape with a predetermined width. This rectangular hole 20d corresponds to the measuring passage 12. Opposite ends 20f and 20g of the rectangular hole 20d are communicated with the passage 1, and the opening of the rectangular hole 20d is closed from the front side and the rear side by the respective holding sections 20a and 20b.

At this time, the thin plate 20c and the holding sections 20a and 20b are attached so that the tip end array of the respective fibers with tip end portions arranged on the respective holding sections 20a and 20b, are arranged along the longitudinal direction of the rectangular hole 20d. FIG. 3 (c) is a cross-sectional view on line A-A of FIG. 3 (a). FIG. 3 (d) is a cross-sectional view showing the vicinity of the measuring points 13 and the illumination points 17 of the attachment jig 20 enlarged.

The length of the rectangular hole 20d is for example of the order of approximately 10 mm, and the width is formed for example to approximately 0.01 mm. The transmission core diameter of the respective optical fibers is for example of the order of 0.01 mm.

Furthermore, the illumination side holding section 20a and the light receiving side holding section 20b, are provided so as to sandwich from left and right, the thin plate 20c which has a thickness of approximately 0.01 mm so that the optical axes of the respective fibers 15 and 18 coincide within a predetermined error range (in this case, a range of ±0.0005 mm) determined from the size of the small objects. Therefore, the cross section of the measuring passage 12 becomes a square or rectangular shape with length and breadth approximately 0.01 mm. The thickness of the respective holding sections 20a and 20b themselves is for example approximately 10 mm.

According to this example, the tip ends of the light receiving fibers 15 and the illumination fibers 18 are able to directly contact with the liquid inside the measuring passage 12, and the light from inside the measuring passage 12 is directly received. Furthermore, the light can be directly shone to inside the passage. As a result, optical noise is prevented, enabling highly accurate measurement.

The passage 11 is not limited to the case where this is bent to an approximate right angle to the slit shape hole 25d corresponding to the measuring passage 12, to communicate or connect with this, and the passage 11 may be the case where this communicates or connects in a straight line with the slit shape hole 25d without being bent. In this case, an unreasonable force due to the passage is not applied to the liquid passing through the passage, and hence control of the velocity or the position is simplified with reliability.

FIG. 4 shows in detail an attachment jig 120 according to another example of the optical measuring unit of this embodiment.

The attachment jig 120 according to this example is one where, different to the aforementioned example, this is suitable to the case of a tube where a measuring passage 121 is formed from a translucent material. As shown in FIG. 4 (a), the attachment jig 120 comprises; an illumination side holding section 120a which holds the illumination fibers 18, a light receiving side holding section 120b which holds the light receiving fibers 15, and a measuring passage protective section 120c of a laminated shape, in which a tubular measuring passage 121 formed from a translucent material is embedded.

This measuring passage protective section 120c is formed by extruding the tubular measuring passage 121, and then subjecting this to an integrated molding process with a resin of the same refractive index as the measuring passage 121. The illumination side holding section 120a and the light receiving side holding section 120b form the connector for the optical fiber.

FIG. 4 (b) is an exploded view showing the attachment jig 120 disassembled. Here reference symbol 122 denotes a thin film protective mould section formed integral with the measuring passage 121, and made of a material the same as the translucent material of the measuring passage 121 or with the same refractive index.

Reference symbol 123 denotes an engaging section which engages with and secures the tip end portions of the illumination side holding section 120a and the light receiving side holding section 120b from the front and back. At the approximate center in the thickness direction of the engaging section 123, the protective mould section 122 is extended so as to partition the engaging section 123 into front and rear. The respective ends of the illumination side holding section 120a and the light receiving side holding section 120b protrude from the front and rear and are engaged with and secured to the protective mould section 122, and the end faces thereof contact with the mould section 122.

FIG. 4 (d) is a cross-sectional view showing the vicinity of a certain measurement point 13 and illumination point 17 of the attachment jig 120. Moreover, the length in the longitudinal direction of the measurement passage protective section 120c is for example approximately 20 mm, and the thickness is for example approximately 2 mm. The thickness of the protective mould section 122 is for example approximately 0.1 mm, the inside diameter of the measuring passage 121 is for example approximately 0.01 mm, the outside diameter thereof is approximately 0.03 mm, and the diameter of the light receiving fibers 15 and the illumination fibers 18 is for example approximately 0.01 mm. In order to increase the measurement sensitivity, the diameter of the tip portion of the illumination fibers 18 may be made greater than the diameter of the tip portion of the light receiving fibers 15, so that the light is shone onto a comparatively wide region.

In this example, the tip faces of the light receiving fibers 15 and the illumination fibers 18 are not directly contacted with the side face of the measuring passage 121, but instead light is shone to and received from the liquid inside the measuring passage 121 via the thickness of the measuring passage 121 and the thickness of the protective mould section 122.

FIG. 5 shows in detail an example of target small objects 34 of several kinds which are to be identified by the small object identifying device 10 according to the present embodiment.

FIG. 5 (a) shows an example of small objects 34a, 34b and 34c as the label elements, which serve as carriers capable of supporting the target material which identifies the target small objects 34 by three kinds of sizes of large, medium and small. The size of the diameters are for example 8 μm, 5 μm and 2 μm. In this case, these identify by shading the illumination light, or reflecting the illumination light. Furthermore, the respective small objects 34a, 34b and 34c themselves may be suitable luminescent materials, or these may be objects where the surfaces of the respective small objects are coated by a suitable luminescent material in amounts corresponding to the magnitude of the aforementioned three types. Here the luminescent material is one which emits light of a certain wavelength range of one type.

FIG. 5 (b) shows an example of a small object 34b serving as a carrier of an intermediate diameter size as shown in FIG. 5 (a), luminescent materials $A_1$, $A_2$ and $A_3$ serving as label elements having three different kinds of wavelength regions capable of being excited by the excitation light of one kind, are bonded to the small object 34b serving as a carrier, using supports 34d of a single chain DNA material or the like bonded to the target material or capable of bonding thereto. In this figure, if the amounts (masses) of the single label elements are assumed equal (actually, these amounts differs for each of the respective label elements, however these are assumed equal for simplicity of explanation), then the molar ratio of $A_1$, $A_2$ and $A_3$ in relation to the small object 34e becomes 1:1:1.

FIG. 5 (c) shows a substance which is labeled by bonding fluorescent substances $B_1$, $B_2$ and $B_3$ serving as label elements having three kinds of different wavelength regions capable of being excited by the excitation light of another kind, to the small object 34b serving as a carrier using supports 34d of for example another single chain DNA material. If the amounts of the single label elements are assumed equal, then the molar ratio of $B_1$, $B_2$ and $B_3$ in relation to the small object 34f also becomes 1:1:1.

FIG. 5 (d) shows a substance which is labeled by fluorescent substances $C_1$, $C_2$ and $C_3$ serving as label elements having three kinds of different wavelength regions capable of being excited by the excitation light of again one kind, on the surface of the small object 34c serving as the carrier of the maximum diameter size of FIG. 5 (a). If the amount of the respective one kinds are assumed equal, then the molar ratio in relation to the small object 34g also becomes 1:1:1.

FIG. 5 (e) shows an example of another kind of small object 34h which is labeled by optionally combining these. Here, if the amounts of the respective label elements are assumed equal, then the molar ratios of the respective label elements in relation to the small object 34h become $A_1:A_2:A_3=1:2:1$, $B_1:B_2:B_3=1:1:2$ and $C_1:C_2:C_3=2:1:1$.

Regarding the above four kinds of label elements shown in FIG. 5, the large size label elements are three kinds, and if it is assumed that the molar ratio of the fluorescent substances $A_{123}$, $B_{123}$ and $C_{123}$ serving as the label elements can each be four kinds (an amount of 0, 1, 2 or 3), then for the kinds of small objects, this gives $3 \times 4^3 \times 4^3 \times 4^3 = 786432$ kinds present.

Figure 6:
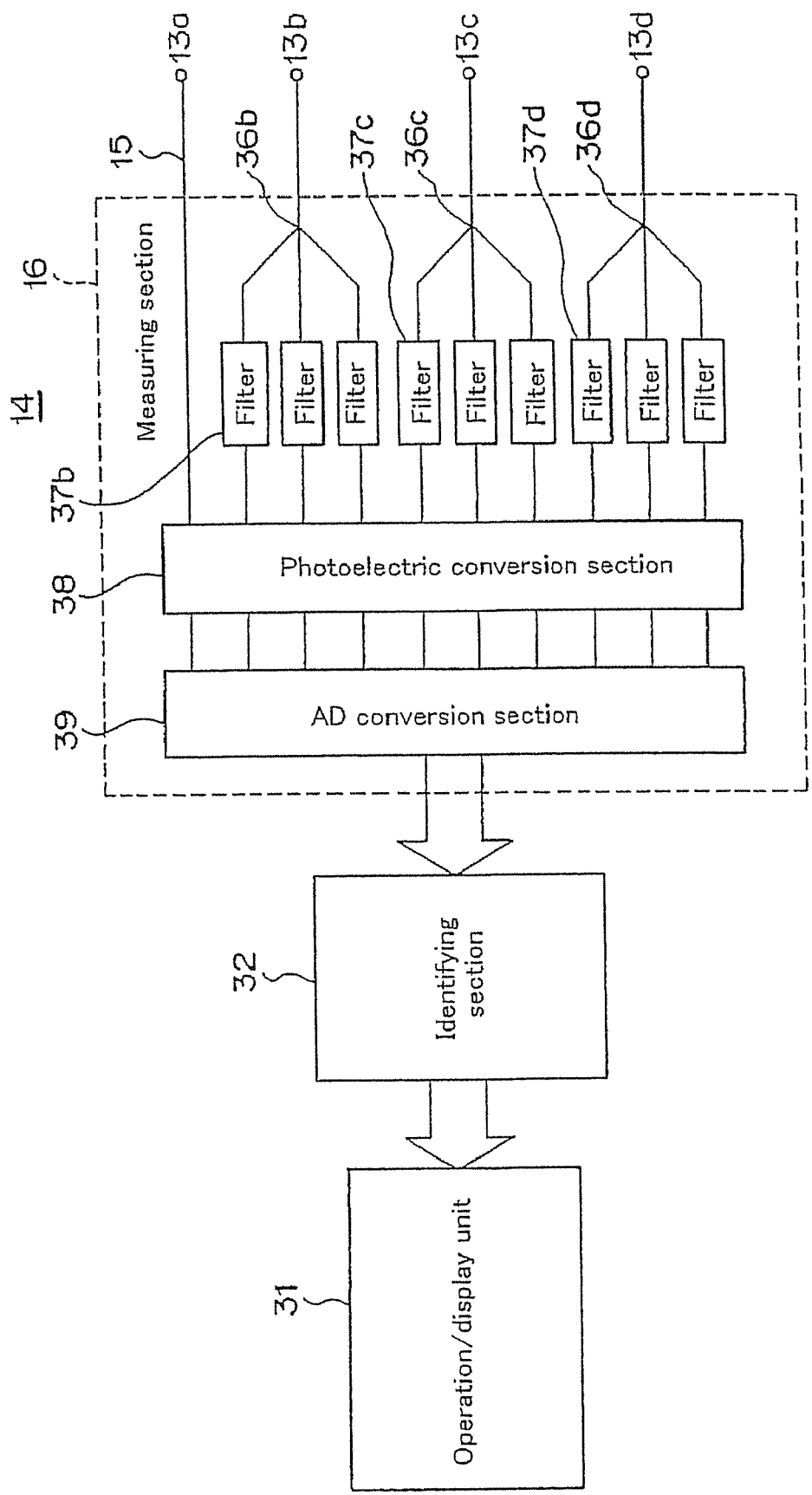
FIG. 6 is a view showing a measuring section and the vicinity thereof, of an optical measuring unit according to the first embodiment of the present invention.

FIG. 6 shows in detail the measuring section 16 of the optical measuring unit 14 which is necessary in the case of identifying the small objects exemplified in FIG. 5.

The measuring section 16 comprises; a photoelectric conversion section 38 which takes in light directly from the light receiving fibers 15 fixedly provided at the four measurement points 13a, 13b, 13c and 13d, or by means of for example four optical fibers via branch points 36b, 36c and 36d and various filters 37b, 37c and 37d, and converts this into analog electrical signals having a voltage value of a magnitude corresponding to the strength of this light, and an AD conversion section 39 which converts these analog electrical signals into digital signals corresponding to the voltage value.

Concerning the first measuring point 13a in FIG. 6, this determines the magnitude of the particles of FIG. 5 (a), and is able to receive light in a wavelength range for one kind of the luminescent material. Concerning the second measuring point 13b, this measures the presence/absence and the measure of the identifying substance in the three kinds of $A_1$, $A_2$ and $A_3$, and is set at a position facing the illumination point 17 which illuminates common excitation light of one kind.

Furthermore, the light receiving fiber 15 has a branch point 36b, and is provided with filters 37b for extracting different wavelength ranges of the aforementioned three kinds of $A_1$, $A_2$ and $A_3$. Moreover, a measuring point 13 is provided at a position facing the illumination point 17 which illuminates common excitation light of one kind. The third measuring point 13c is for measuring the presence/absence and the measure of the three kinds of identifying substances of $B_1$, $B_2$ and $B_3$. The light receiving fiber 15 has a branch point 36c, and has filters 37c for extracting different wavelength ranges of the three kinds of $B_1$, $B_2$ and $B_3$.

The fourth measurement point 13d is for measuring the presence/absence and the measure of the $C_1$, $C_2$ and $C_3$. The light receiving fiber 15 also has a branch point 36d, and is provided with filters 37d for extracting different wavelength ranges of the three kinds of $C_1$, $C_2$ and $C_3$. Moreover, the measurement points 13 are provided at positions corresponding to the illumination points 17 which illuminate common excitation light of one kind.

The AD conversion section 39 outputs a digital signal corresponding to the strength of light received for each of the measurement points, synchronized with a predetermined time interval which is determined based on the relative velocity, that is, in this example, based on the flow velocity. The identifying section 32 identifies the kind of the target small object by relating the digital signals of the respective measurements points to each other, based on the position coordinates of the measurement points, and the time interval of the digital electrical signals output from the respective measurement points. The measurement results are sent to the operation/display unit 31, and displayed on a display device or the like.

Here, instead of providing the AD conversion section, the waveforms of the photoelectrically converted electrical signal may be recorded as is, and the waveforms of the temporal fluctuations in the strength of the light which is received in the respective measurement points, may be mutually related based on the relative velocity, to thereby identify the kind of the target small object.

In identifying small objects using the small object identify device and method thereof according to the present embodiment, when the operator inputs the operating instructions to the operation/display unit 31, the three-way valves 26a, 25 and 26 switch the passage 11 by means of the mechanism control section 30, so that the suction nozzle 22 is able to draw up liquid. Then by means of the suction discharge unit 28, the target liquid contained in the container 21, and the liquid of a comparatively small amount in which is suspended the reference small objects are drawn up by means of the suction nozzle 22, and are carried as far as the suction/ejection mechanism 28 side past the three-way valve 26. Then, the three-way valve 25 and the three-way valve 26 are switched so that the water stored in the water flow tank 23 is drawn out by the transport pump 24, and this water and the liquid which suspends the target small object are mixed, and the mixed water is passed through the measuring passage 12 by means of the transport pump 24.

At this time, excitation light having a predetermined wavelength is shone from the light source section 19 onto the illumination points 17 via the illumination fibers 18, and the light from the passing small objects is received by the light receiving fibers 15 provided at the measurement points 13, and the received light is measured by the measuring section 16, and the small objects 34 are identified by the identifying section 32. After passing through the measuring passage 12, the passed mixed water is discarded to the waste tank 27.

Next, by switching the three-way valves 26a, 26 and 25, cleaning solution is drawn up from the container 21a, and as mentioned above, the water mixture of cleaning solution and water is passed through the measuring passage 12 to thereby completely remove small objects from inside the passage 11. Moreover, by switching the three-way valve 26a so as to discharge the water mixture from the suction nozzle 22, the small objects inside the suction nozzle 22 are completely removed, ready for the next measurement.

Figure 7:
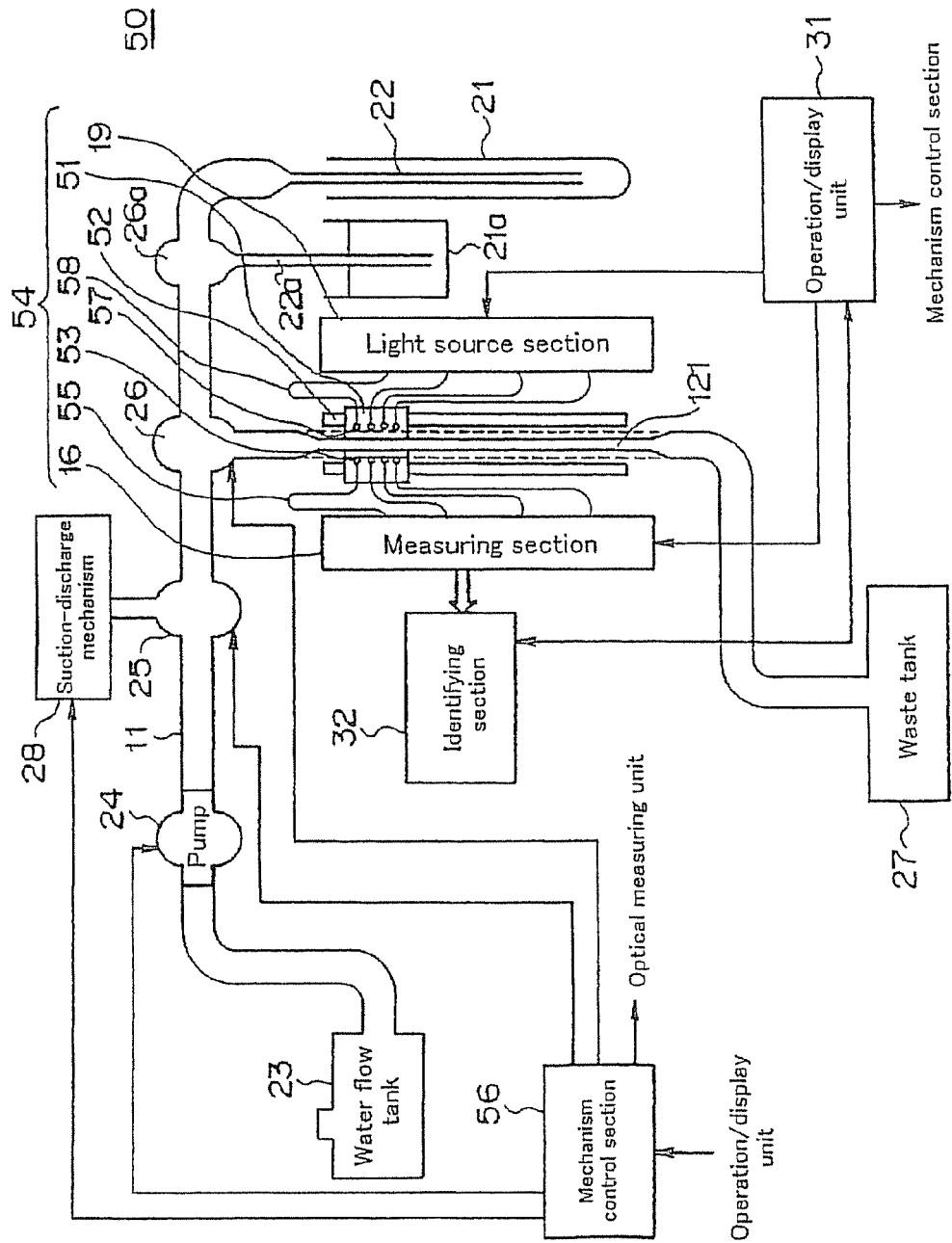
FIG. 7 is an overall conceptual diagram of a small object identifying device according to a second embodiment of the present invention.

FIG. 7 shows the whole of a small object identifying device 50 according to a second embodiment. Here the same symbols as for the small object identifying device 10 according to the first embodiment described in FIG. 1 denote the same parts, and description thereof is omitted.

With this small object identifying device 50, instead of the optical measuring unit 14 according to the first embodiment, there is provided an optical measuring unit 54 which instead moves the measurement points and the illumination points with respect to the liquid accumulated inside the measuring passage 121, to thereby perform measurement.

With this optical measuring unit 54, there is provided a carriage 51 which is guided on two straight rails 52 provided along the measuring passage 121, and is thus moveable along the measuring passage 121. The carriage 51 has a plurality of light receiving fibers 55 serving as light receiving sections with tip portions attached by an attachment jig (not shown in the figure) to a plurality of (in this example 4) measurement points 53 which are arranged along the movement direction, and illumination fibers 58 serving as illumination sections with tip portions thereof attached by means of an attachment jig (not shown in the figure), so that excitation light for a plurality of illuminating points 57 (in this example four) also arranged along the movement direction of the carriage 51 are able to be shone towards the respective measurement points 53 with the measuring passage 121 sandwiched therebetween.

Here, for the attachment jig, there is for example one where as shown in FIG. 4, the light receiving side holding section which holds the light receiving fiber and the illumination side holding section which holds the illumination fiber are secured together with the measuring passage 121 therebetween, and attached to the carriage 51.

The light receiving fibers 55 and the illumination fibers 58 must be formed so as to have flexibility or resilience so as not to obstruct movement when the carriage 51 is moved along the measuring passage 121.

Moreover, in the small object identifying device 50 according to this embodiment, there is provided a mechanism control section 56 for controlling the transport pump 24, the three-way valves 25 and 26, the suction/discharge device 28 and the optical measuring unit 54. The carriage 51 corresponds to the movement section. Furthermore, for the identifying section 32 of the small object identifying device 50 according to this embodiment, the predetermined relative velocity becomes the movement velocity of the carriage 51.

FIG. 8(a) shows an example of the measuring passage 121 of the optical measuring unit 54 according to the second embodiment shown in FIG. 7.

A liquid 62 which is introduced to the passage 11 from the container 21 is controlled so as to flow inside the measuring passage 121 alternately with a buffer liquid 63 which is supplied from the water flow tank 23, and measurement is performed by moving the carriage 51 along the measuring passage 121 in a condition with these accumulated inside the measuring passage 121.

FIG. 8 (b) shows another example of the measuring passage 121 of the optical measuring unit 54 according to the second embodiment. In this example, this is secured and attached by means of the attachment jig (not shown in the figure) to the carriage 61, in a condition with the measurement points 53, the illuminating points 57 and the light receiving fibers 55, and the illumination fibers 58, provided so that the optical axes of the tip portions of the light receiving fibers 55 and the optical axes of the tip portions of the illumination fibers 58 intersect at a predetermined angle at the central axis within the measuring passage 121. This plurality (in this example 4) of measurement points 53 and illumination points 57 are arranged along the movement direction of the carriage 61.

Furthermore, in order to increase the measurement sensitivity, the diameter of the tip portion of the illumination fibers 58 may be made greater than the diameter of the tip portion of the light receiving fibers 55, so that light is shone onto a comparatively wide region.

In this example, the liquid 33 for which the high density suspension which suspends the target small object and which is introduced to the measuring passage 121, is mixed with the water from the water flow tank 23 and diluted, is accumulated inside the measuring passage 12 by operating the transport pump 24 and the suction/discharge device 28. In this condition, measurement is performed by moving the carriage 61 at a predetermined movement velocity along the approximate tube shape measuring passage 121.

Figure 9:
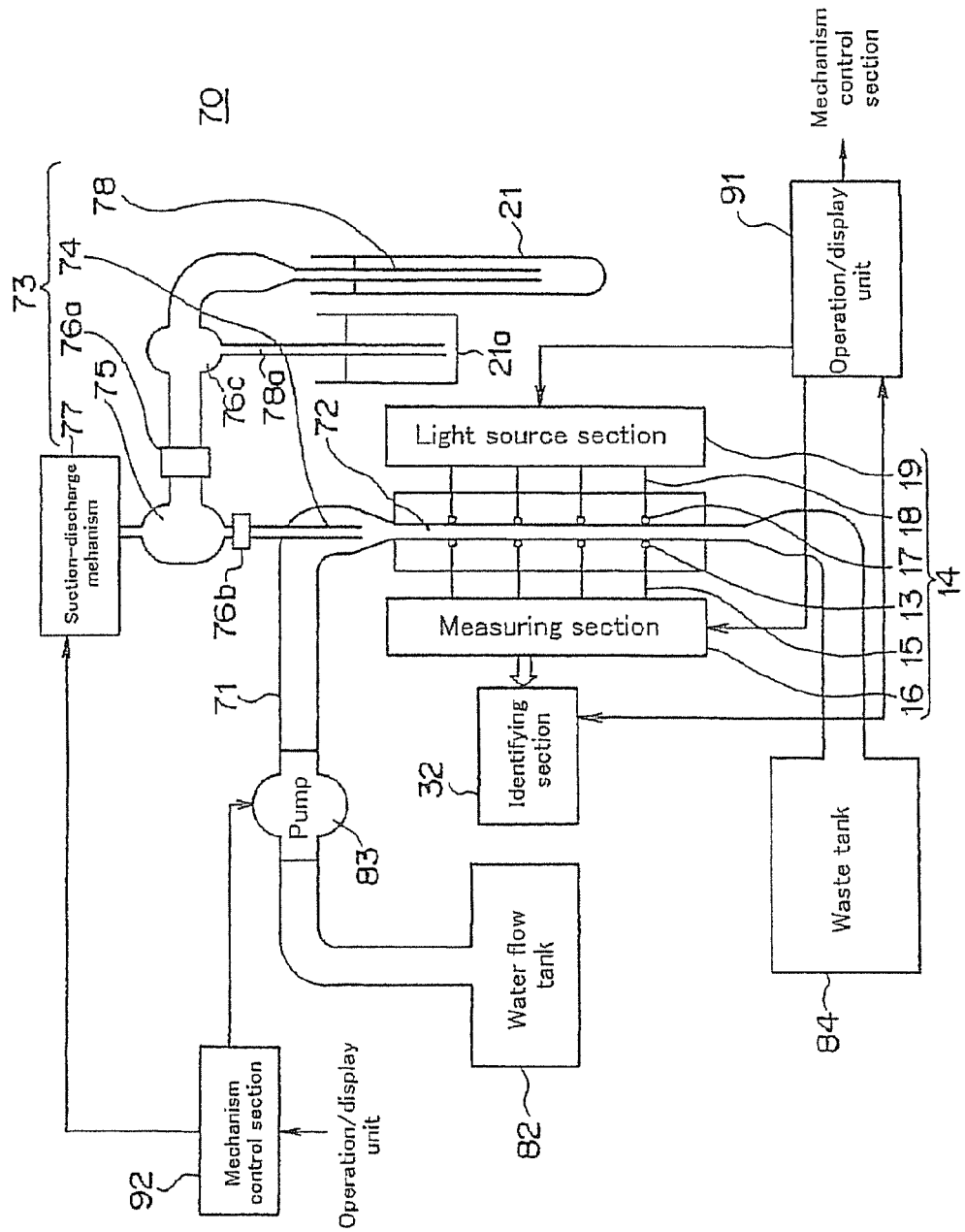
FIG. 9 is an overall conceptual diagram of a small object measuring unit of a small object identifying device according to a third embodiment of the present invention.

Next a small object identifying device 70 according to a third embodiment is described based on FIG. 9. Reference symbols the same as in FIG. 1 denote the same parts, and description thereof is omitted.

In the small object identifying device 70 according to this embodiment, instead of the passage 11 according to the first embodiment, when the suspension liquid which suspends the small objects is introduced, rather than being immediately mixed with the liquid from the water flow tank 82, the suspension liquid is introduced to inside the passage 71 using a liquid introducing device 73.

This uses a passage 71 which temporarily accumulates water, and which is provided with the liquid introducing device 73 for mixing by discharging an amount of suspension liquid, corresponding to instructions, into the water flow. A part of this passage 71 constitutes the measurement passage 72.

In this embodiment, the liquid introducing device 73 is provided with; a suction nozzle 78 for drawing up liquid stored in the container 21 which stores liquid containing the small objects, a reservoir section 75 which accumulates the drawn up liquid, a discharge nozzle 74 with the tip provided inside the passage 71 and which discharges liquid accumulated in the reservoir section 75, a suction-discharge mechanism 77 which draws up liquid stored in the container 21 from the suction nozzle 78 and discharges this from the discharge nozzle 74, and diverter valves 76a and 76b which can be switched over to a non return direction for switching the suction nozzle 78 and the discharge nozzle 74. Preferably the discharge nozzle 74 is provided so as to be freely detachable with respect to the passage 71.

Figure 10:
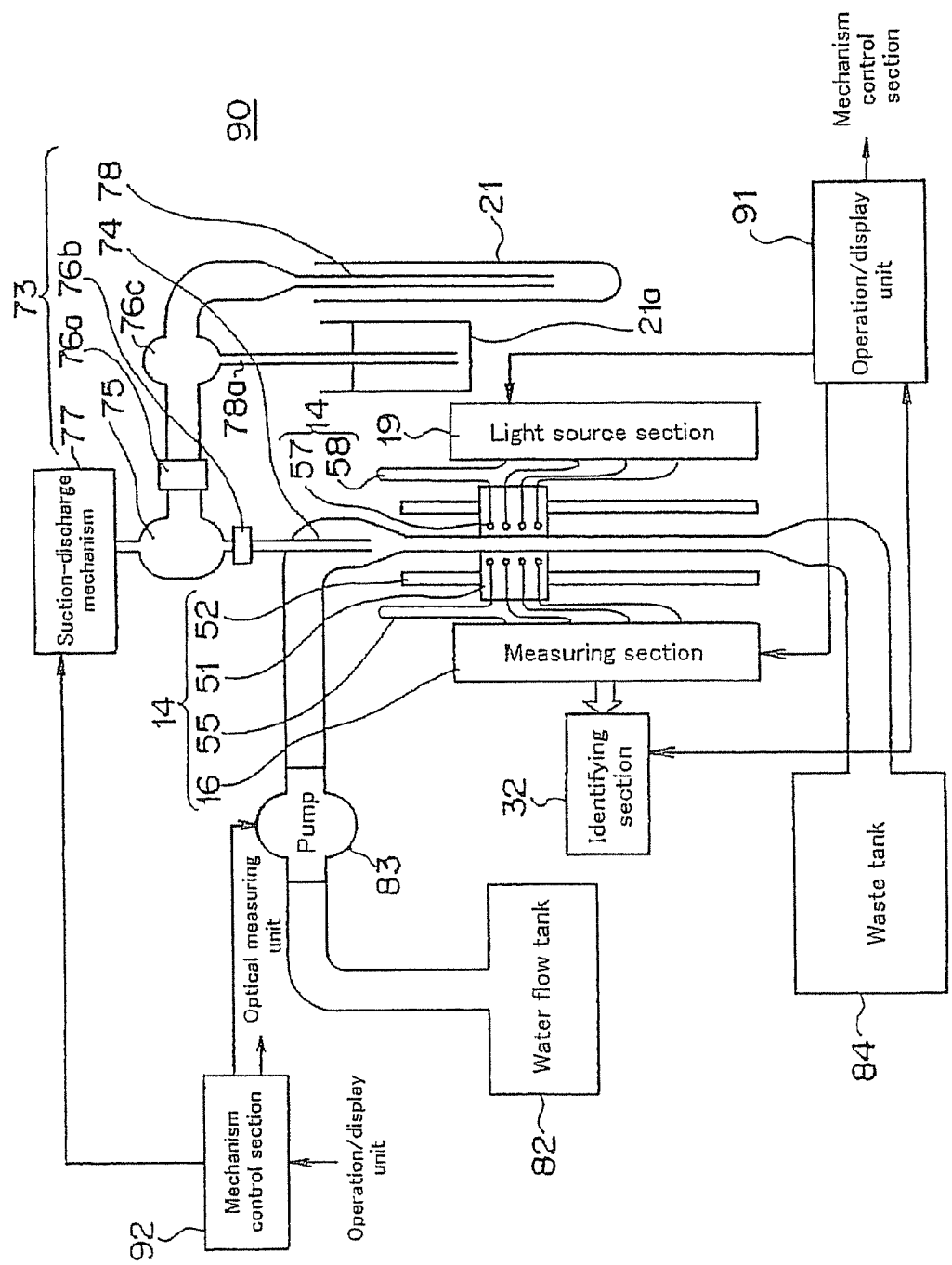
FIG. 10 is an overall conceptual diagram of a small object identifying device according to a fourth embodiment of the present invention.

The discharge nozzle 74 is provided coaxially on the approximate center of the passage 71, and by flowing water from the passage 71, the liquid discharged from the discharge nozzle 74 can also be flowed so as to form a core flow inside the water flow. At this time, the diameter of the discharge nozzle 74 is formed so as to be sufficiently finer compared to that of the passage 71. In the fluid (core flow) from the discharge nozzle 74 is contained the small objects drawn up from the container 21, and in the passage 71 flows a fluid (source flow) which does not contain the small objects. The measurement passage 72 is provided so as to be on the down stream side of the core flow injection tip of the discharge nozzle 74. At the point below the core flow injection tip it is preferable to have an inclined plane of a conical shape where the cross section area of the passage 71 gradually reduces along the flow direction of the fluid as shown in FIG. 9 and FIG. 10 (a neck down region). What needs to be most avoided in this region is a shape which produces turbulence. As the cross section area decreases, the flow velocity increases, and the proportion of the cross section area of the core flow with respect to the cross section area of the source flow changes in accordance with the relative volumetric flow rate between the source flow and the core flow. As a result, the flow in the measurement passage 72 is stabilized, and can be adjusted so that for example the small objects pass the measurement points one at a time.

Moreover, in the small object identifying device 70 according to this embodiment, there is provided a mechanism control section 80 for controlling the diverter valves 76a and 76b, the suction-discharge mechanism 77, and the transport pump 83. Furthermore, there is provided an operation/display unit 81 which executes operation or instructions and display for the optical measuring unit 14 and the mechanism control section 80.

In this embodiment, the liquid which suspends the small objects 34 and 35 discharged from the discharge nozzle 74 is passed at a predetermined velocity so that this alternates with the buffer liquid region from the water flow tank 82. Moreover, the liquid which suspends the small objects 34 and 35 discharged from the discharge nozzle 74 is controlled so that this is uniformly mixed with the liquid from the water flow tank 82, and when this flows at a predetermined velocity, measurement of the respective small objects 34 and 35 in the measuring passage 12 is performed.

FIG. 10 describes a small object identifying device 90 according to a fourth embodiment. Reference symbols the same as in the aforementioned figures denote the same parts, and description thereof is omitted.

In the small object identifying device 90 according to this embodiment, instead of the optical measuring unit 14 which is used in the small object identifying device 70 according to the third embodiment, an optical measuring unit 54 is used. Furthermore, in this device 90, there is provided a mechanism control section 92, and control of the mechanisms is performed with respect to the suction-discharge mechanism 77, the transport pump 83, and the optical measuring unit 54. This mechanism control section 92 is driven by operating instructions from the operation/display unit 91.

Figure 11:
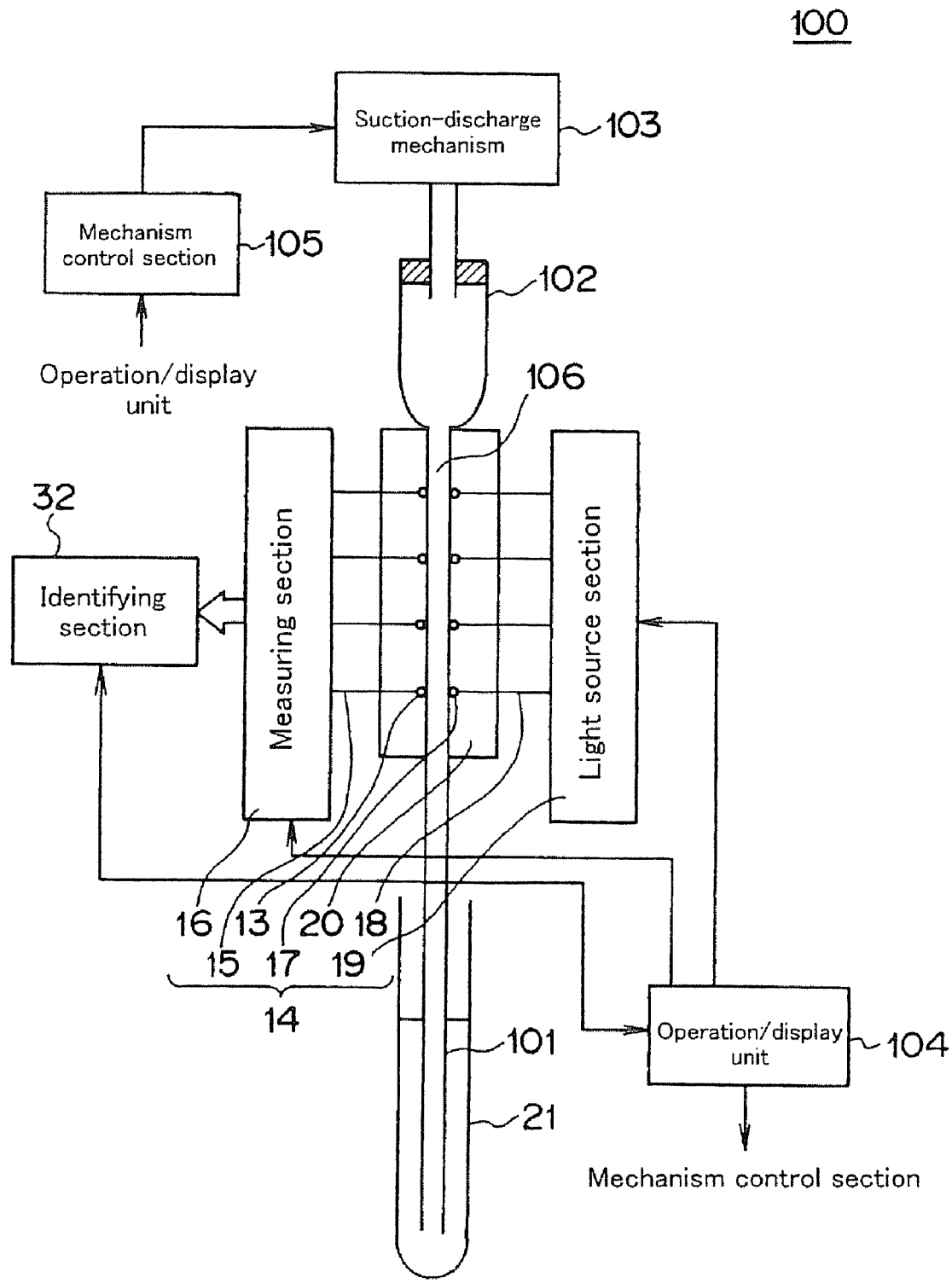
FIG. 11 is an overall conceptual diagram of a small object identifying device according to a fifth embodiment of the present invention.

FIG. 11 describes a small object identifying device 100 according to a fifth embodiment. Reference symbols the same as the reference symbols shown in the aforementioned figures denote the same parts, and description thereof is omitted.

The small object identifying device 100 according to this embodiment comprises; a nozzle tip section 101 which store liquid which suspends the target small objects, and which is inserted into a container 21 provided on the outside of the device 100, a reservoir section 102 which accumulates the drawn up liquid, a measuring passage 106 formed between the nozzle tip section 101 and the reservoir section 102, which is at the upper portion of the nozzle tip section 101, and which performs measurement of the small objects, and a suction-discharge mechanism 103 communicated with the reservoir section 102 for performing suction and discharge of the liquid.

On the side face of the measuring passage 106 there is arranged a plurality (in this example 4) of measurement points 13 which are fixedly arranged along the flow direction. The optical measuring unit 14 has been already described, and hence here description is omitted. Furthermore, a mechanism control section 105 performs control for the suction-discharge mechanism 103 based on instructions from an operation/display section 104.

Figure 12:
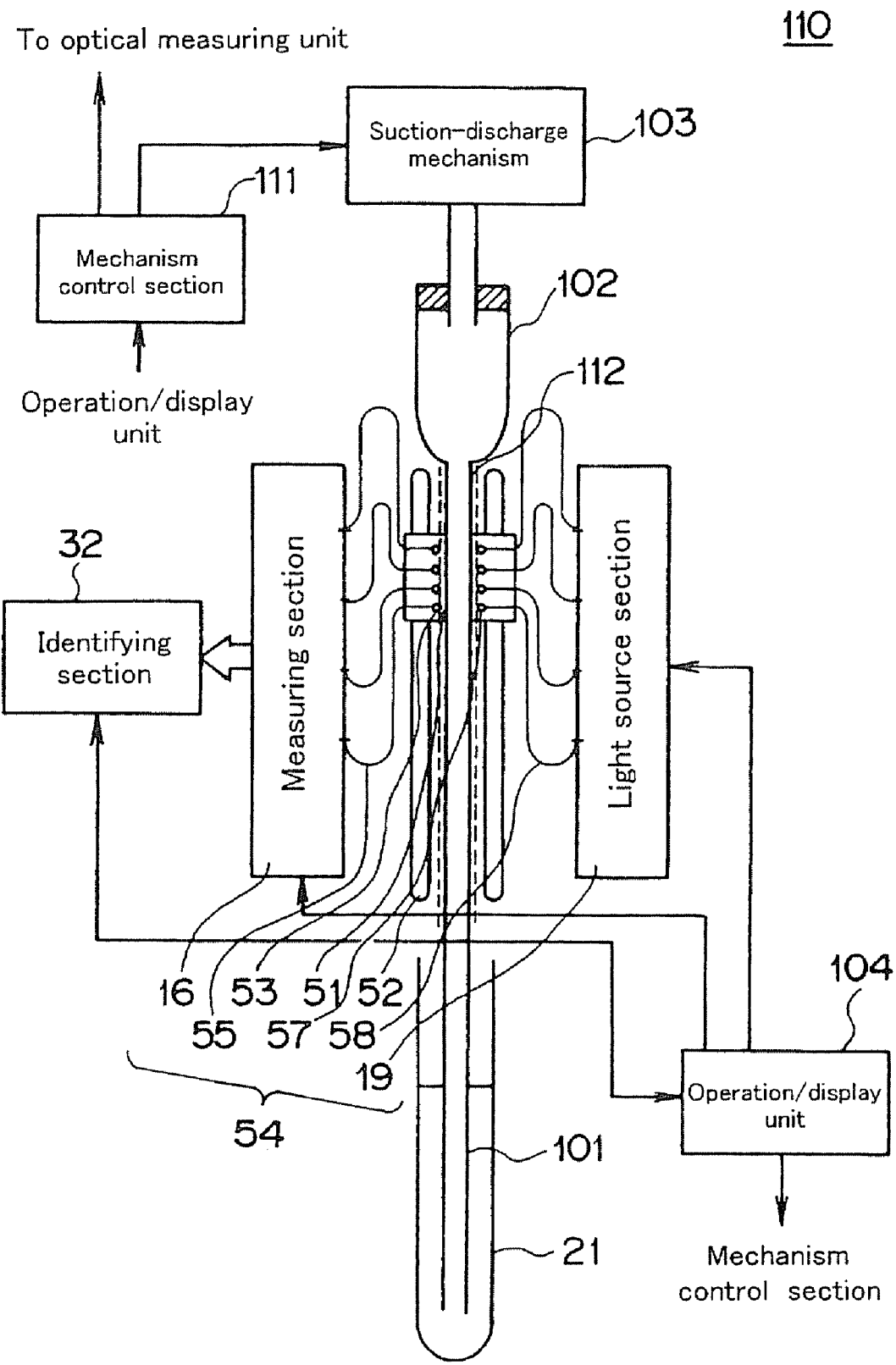
FIG. 12 is an overall conceptual diagram of a small object identifying device according to a sixth embodiment of the present invention.

FIG. 12 describes a small object identifying device 110 according to a sixth embodiment. Reference symbols the same as those shown in the aforementioned figures denote the same parts, and description thereof is omitted.

In the small object identifying device 110 according to this embodiment, instead of the optical measuring unit 14 of the small object identifying device 100 according to the fifth embodiment, there is provided an optical measuring unit 54 which can move the measurement points 53 with respect to the liquid accumulated inside the measuring passage 112. The optical measuring unit 54 has already been described, and hence here description is omitted.

Figure 13:
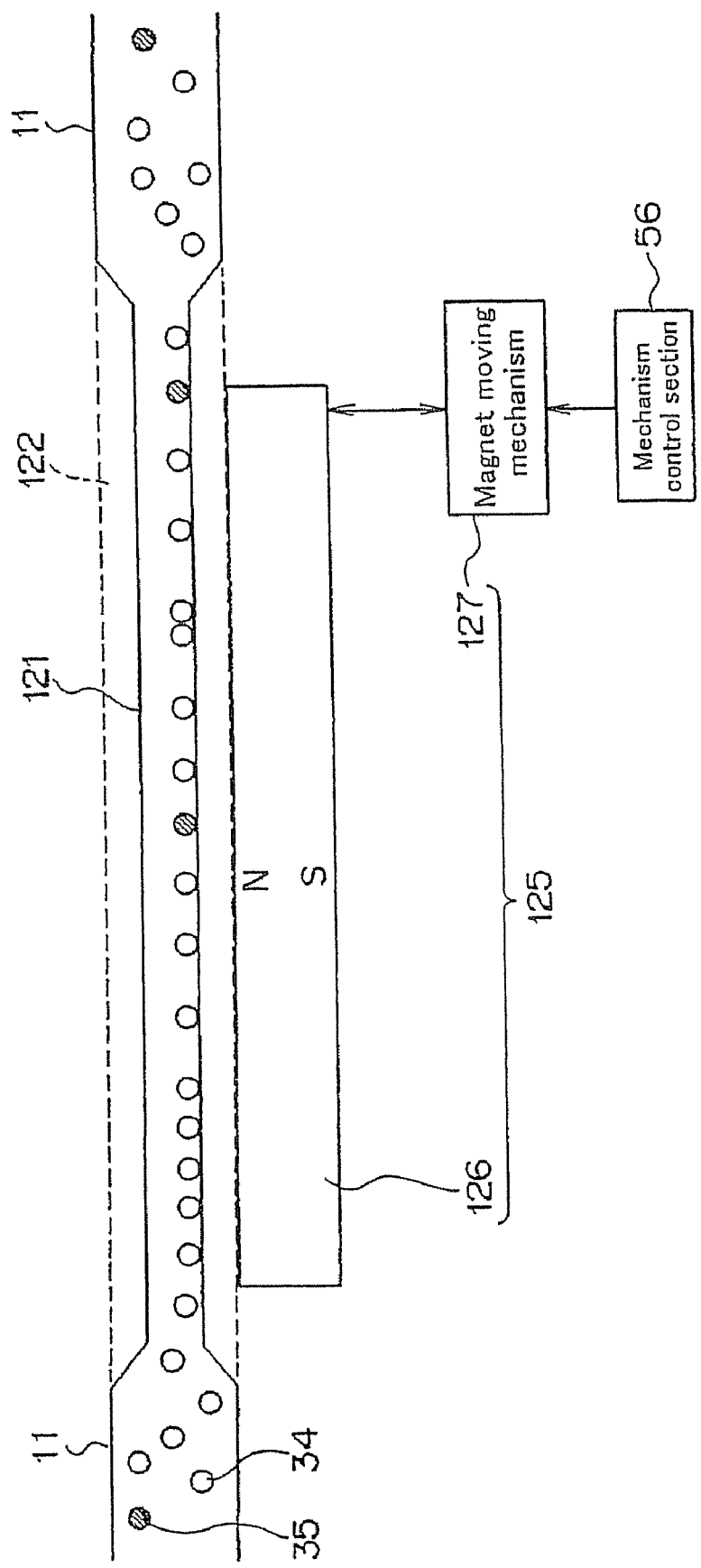
FIG. 13 a conceptual diagram showing a magnetic unit according to a seventh embodiment of the present invention.

Next is a description of a magnetic device 125 according to a seventh embodiment, based on FIG. 13.

The magnetic device 125 according to this embodiment comprises; a magnet 126 which is provided so as to be able to be brought close to and separated from the measuring passage 121 of the small object identifying device 50 according to the second embodiment, and a magnet moving mechanism 127 for bringing close and separating the magnet 126 with respect to the measuring passage 121. The magnet moving mechanism 127 is controlled by the mechanism control section 56.

The magnet 126 is provided so as to move along a direction perpendicular to the optical axes of the light receiving fibers 55 and the illumination fibers 58, so as not to obstruct the movement of the carriage 51 of the optical measuring unit 54.

Instead of the magnet 126 and the magnet moving mechanism 127, there may be provided an electromagnet and a current supply unit which supplies and cuts off current to the electromagnet.

Figure 14:
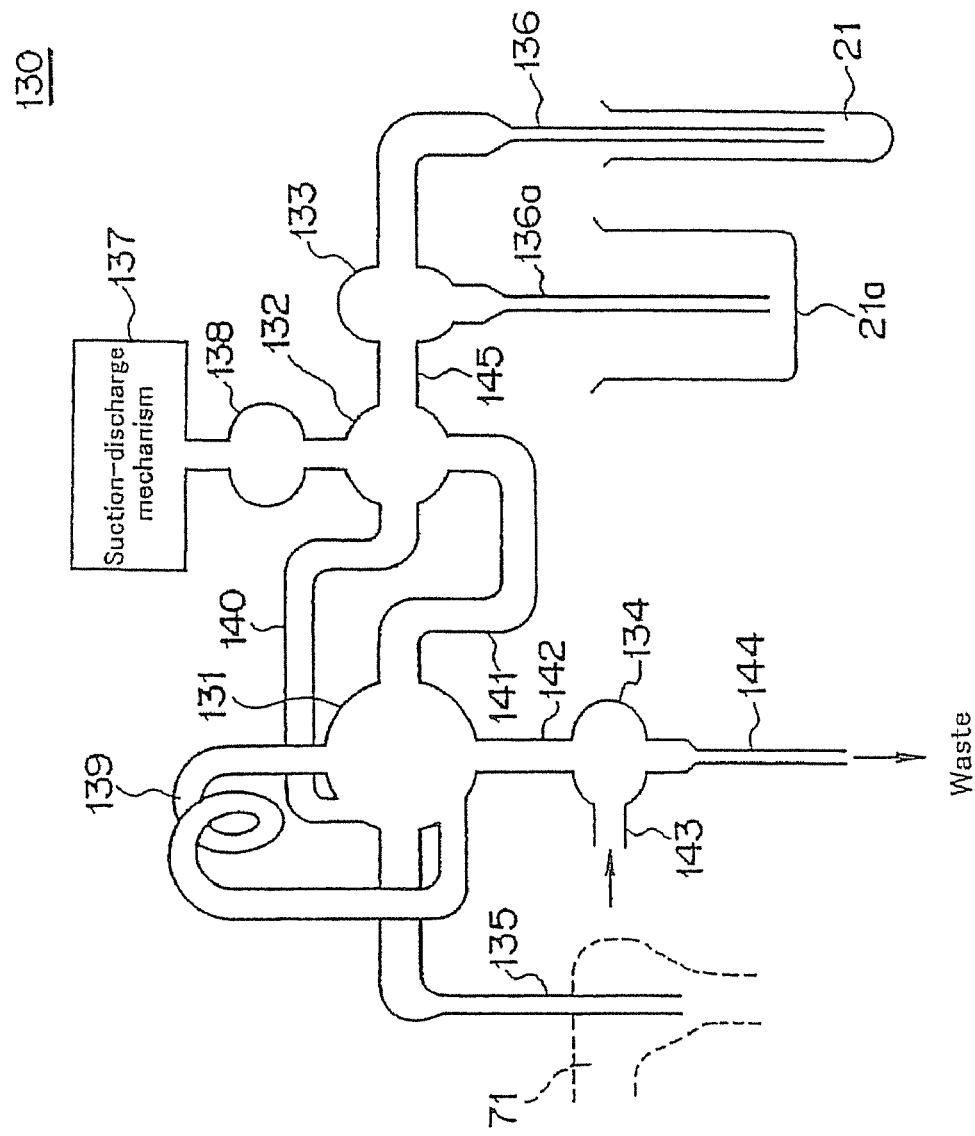
FIG. 14 is a piping diagram showing another example of a liquid introducing device of the small object identifying device according to the third and fourth embodiments of the present invention.

FIG. 14 shows a liquid introducing device 130 according to another example of the liquid introducing device 73 used in FIG. 9 and FIG. 10. The liquid introducing device 130 according to this example, uses a six-way valve 131, a four-way valve 132, and three-way valves 133 and 134 to introduce liquid which suspends the target small object, and cleaning solution, into a passage 71 of the small object identifying device according to this embodiment.

Moreover, this liquid introducing device 130 further comprises; a suction nozzle 136 for drawing up liquid to be introduced from the container 21, a cleaning solution nozzle 136a for drawing up cleaning solution from a container 21a which contains cleaning solution, a discharge nozzle 135 for introducing liquid to the passage 71 of the small object identifying device, a reservoir section 138 for storing the drawn up liquid, a waste nozzle 144 for discharging waste fluid, a sample loop section 139 for measuring the liquid amount, and a suction-discharge mechanism 137 for drawing up and discharging a liquid. These respective elements are connected by respective pipes 140, 141, 142, 143 and 145 so as to be able to move the fluid.

Figure 15:
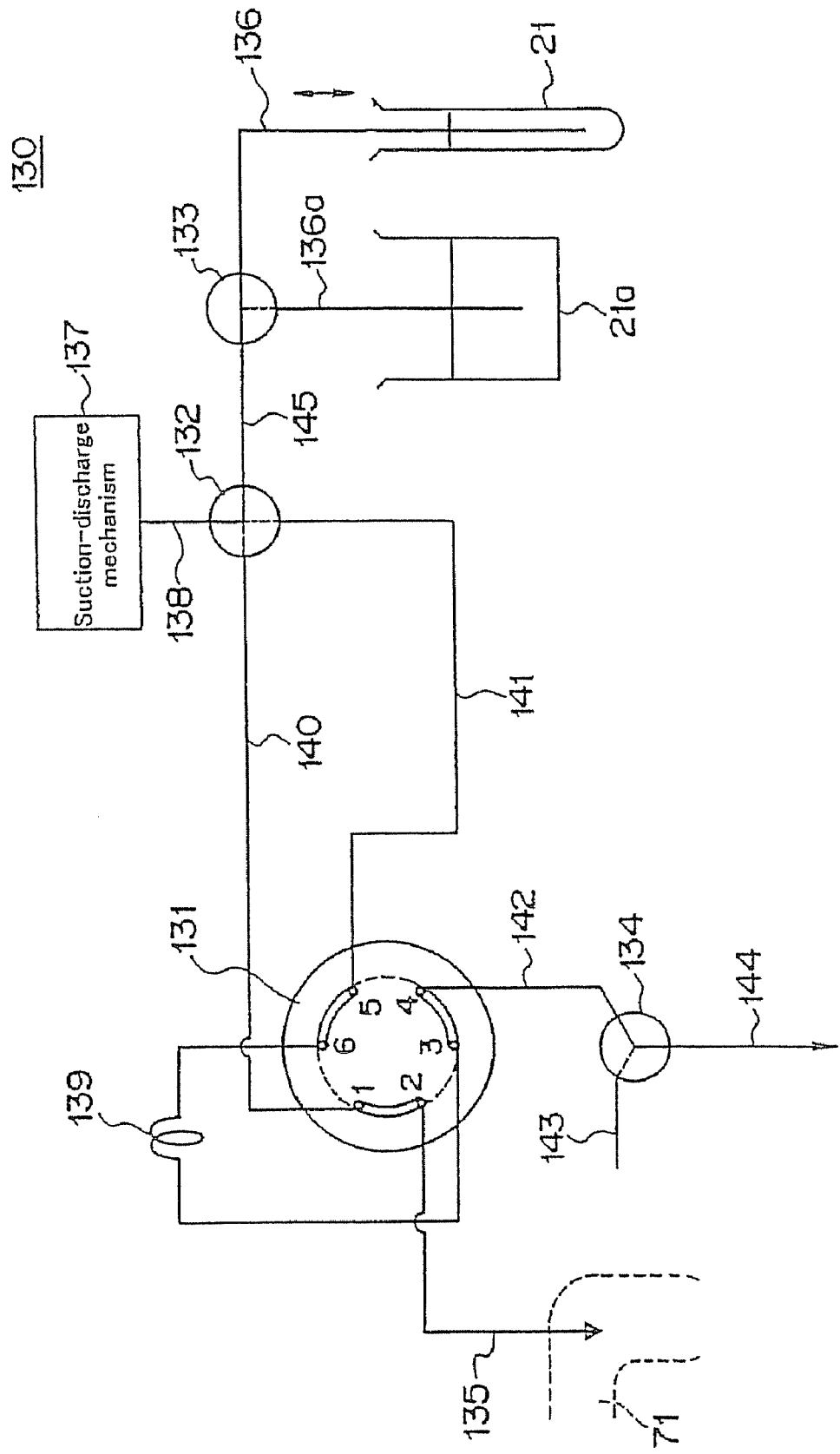
FIG. 15 is a diagram for explaining the operation of the liquid introducing device shown in FIG. 14.

FIG. 15 is a diagram for explaining the operation of the liquid introducing device 130 shown in FIG. 14.

In introducing the liquid to the passage 71 of the small object identifying device, the three-way valve 134 is switched to connect the pipe 142 and the pipe 143, to drawn in extra air by means of a syringe pump serving as the suction-discharge mechanism 137.

The sample comprising the liquid from the container 21 is then drawn up from the suction nozzle 136 by means of the suction-discharge mechanism 137. After drawing up a fixed quantity (up to 10 micro liters), the tip of the suction nozzle 136 is raised by a raising mechanism (not shown in the figure) to a height where it is taken out from the sample. The suction-discharge mechanism 137 again draws in air from the suction nozzle 136, and the sample is moved as far as the reservoir section 138. Due to the presence of this air, the sample is not introduced to inside the cylinder of the suction-discharge mechanism 137, and hence contamination of the cylinder by the sample is prevented.

The four-way valve 132 is then switched to connect the reservoir section 138 and the pipe 141, and by means of the suction-discharge mechanism 137, the sample is filled to inside of the sample loop section 139, and more precise sample quantitative estimation is performed. Next, the six-way valve 131 and the four-way valve 132 are switched to connect the pipe 142 and the waste nozzle 144, and the surplus sample inside the piping of the pipe 141 and the pipe 142 is discharged to the waste tank.

Next, the four-way valve 132 is switched to connect the reservoir section 138 and the pipe 140, and the sample inside the sample loop section 139 is discharged by the suction-discharge mechanism 137 and is introduced to inside the passage 71 of the small object identifying device via the discharge nozzle 135.

Next is a description of the case where washing of the liquid introducing device 130 is performed. In this case, since the condition is such that air already fills the cylinder of the suction-discharge mechanism 137, the three-way valve 133 is switched to connect the cleaning solution nozzle 136a and the pipe 145, and the cleaning solution inside the container 21a is immediately drawn up using the suction-discharge mechanism 137. The four-way valve 132 is then switched to connect the reservoir section 138 and the pipe 140, and cleaning solution is discharged by the suction-discharge mechanism 137 to clean inside of the sample loop section 139. The steps from switching of the three-way valve 133 to cleaning inside the sample loop section 139 are repeated several times.

To continue, the three-way valve 133 is switched to connect the cleaning solution nozzle 136a and the pipe 145, the four-way valve 132 is switched to switch the pipe 145 to the reservoir section 138, and the cleaning solution is drawn up by the suction-discharge mechanism 137. Next, the four-way valve 132 is switched to connect the reservoir section 138 and the pipe 141, the three-way valve 134 is switched to connect the pipe 142 and the waste nozzle 144, and in addition the six-way valve 131 is switched. The cleaning solution is discharged by the suction-discharge mechanism 137 to clean inside of the piping of the pipe 141 and the pipe 142. The steps from switching of the three-way valve 133 to cleaning inside the piping of the pipe 141 and the pipe 142 is repeated several times.

Figure 16:
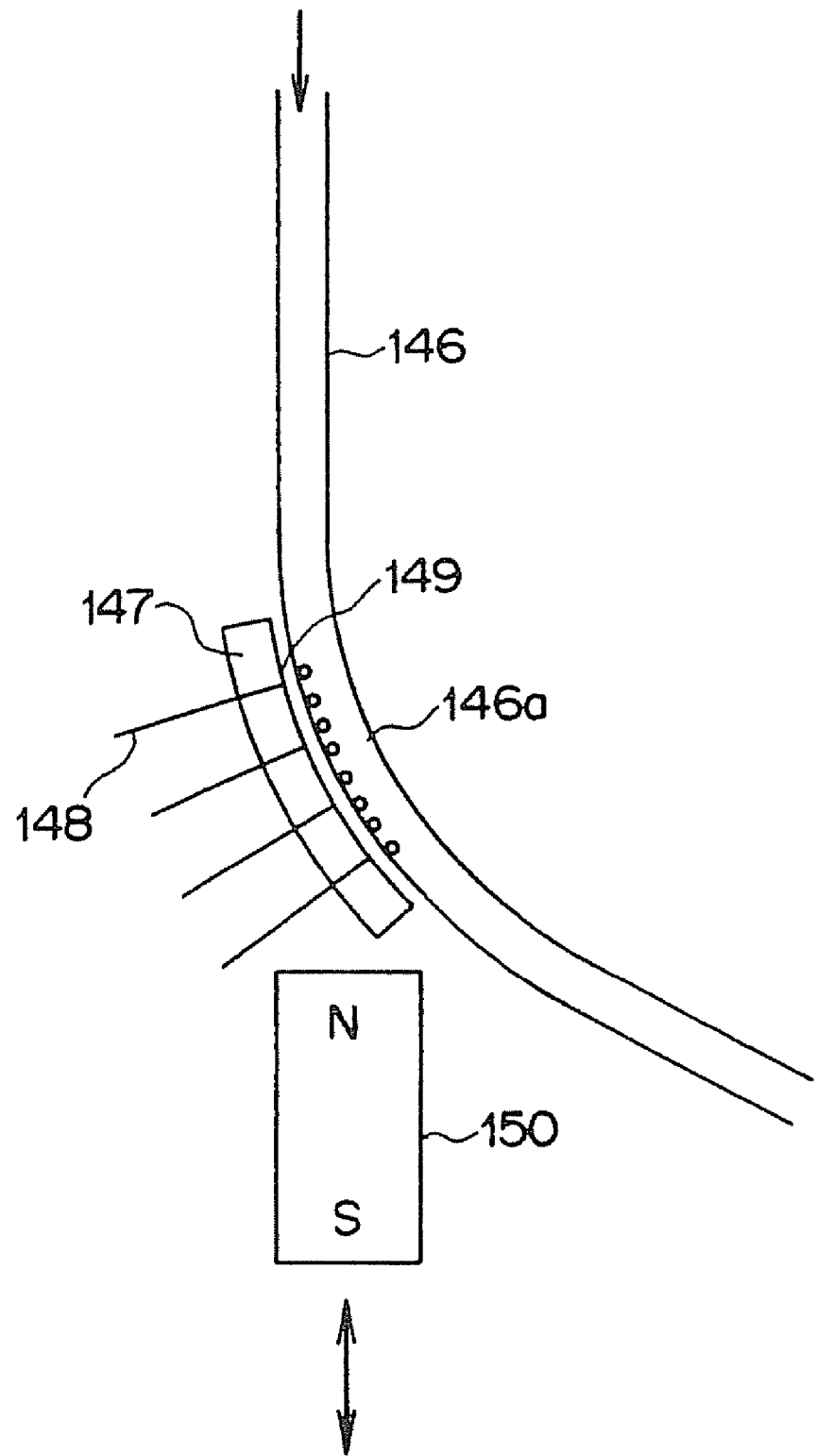
FIG. 16 is a diagram showing a measurement passage according to an eighth embodiment of the present invention.

FIG. 16 shows a passage 146 according to an eighth embodiment. Of this passage 146, a measurement passage 146a which performs measurement is formed bent in a curve. On the non center-of-curvature side of the measurement passage 146a is provided two or more measurement points 149, and on each measurement point 149 is provided a light receiving fiber 148 with a tip, as the light receiving portion. The tip portion of this light receiving fiber 148 is fixedly provided on the outside of the measurement passage 146a by means of an attachment jig 147 which is formed in a curve along the measurement passage 146a.

Furthermore, there is provided a permanent magnet (or an electromagnet) serving as a magnetic force device 150, having a magnetic field direction in the direction of the upstream side passage direction of the measurement passage 146a, and provided so as to be moveable in the upstream side passage direction so as to approach and separate from the measurement passage 146a. The magnetic force device 150 is provided so that in the case where this approaches the measurement passage 146a, a magnetic field of a predetermined strength is exerted on the interior of the measurement passage 146a so that the magnetic particles passing through the measurement passage 146a, pass so as to be lined up along the measurement passage 146a, while in the case where this is separated from the measurement passage 146a, the magnetic field of the predetermined strength is not applied to the interior of the measurement passage 146a, so that this does not have an influence on the magnetic particles.

According to this embodiment, by lining up the magnetic particles passing through the measurement passage 146a as they approach the measurement points 149, the small objects can be accurately measured.

Figure 17:
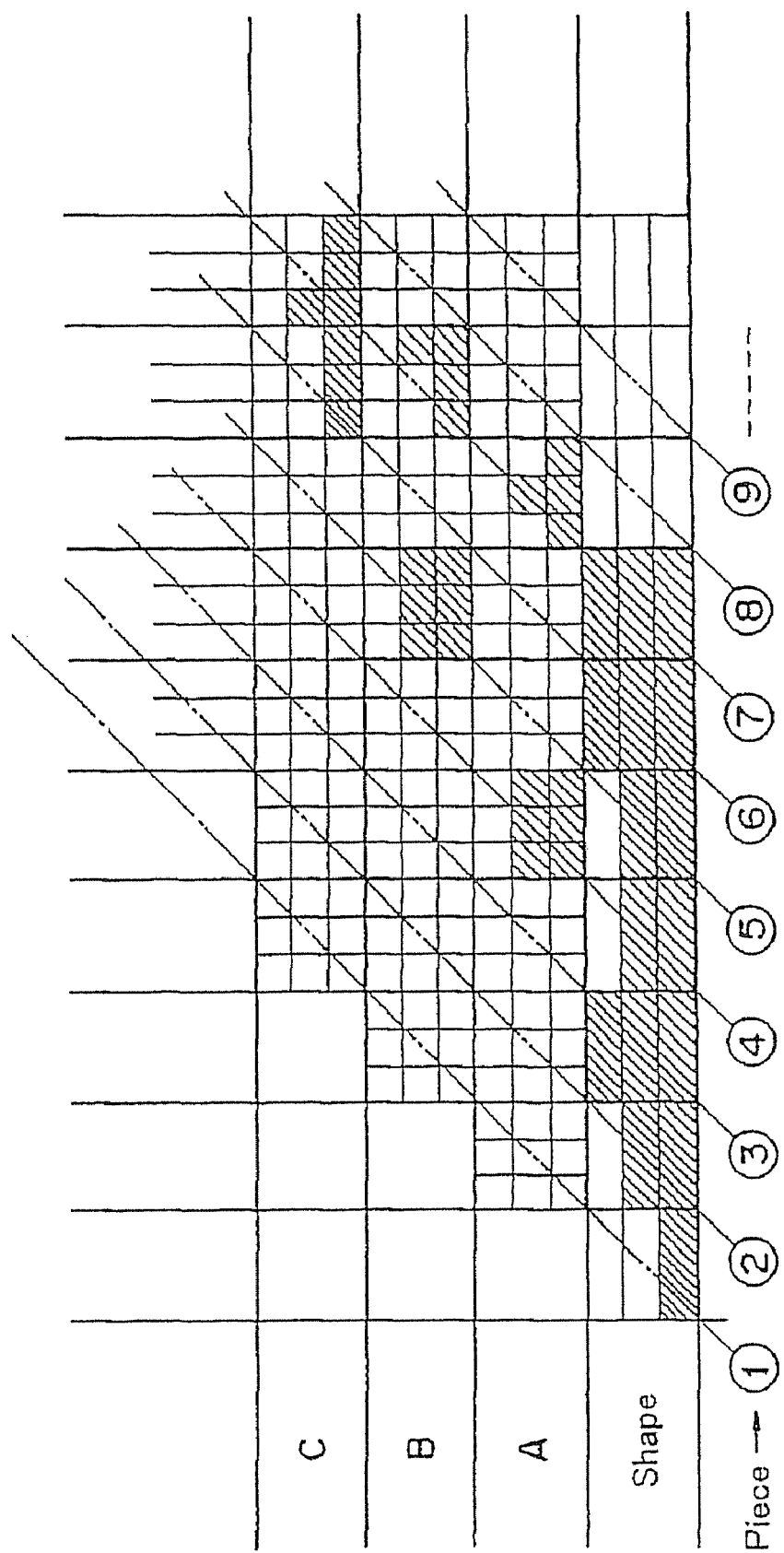
FIG. 17 is a diagram showing measurement results of the small object identifying device according to the first embodiment of the present invention.
Figure 18:
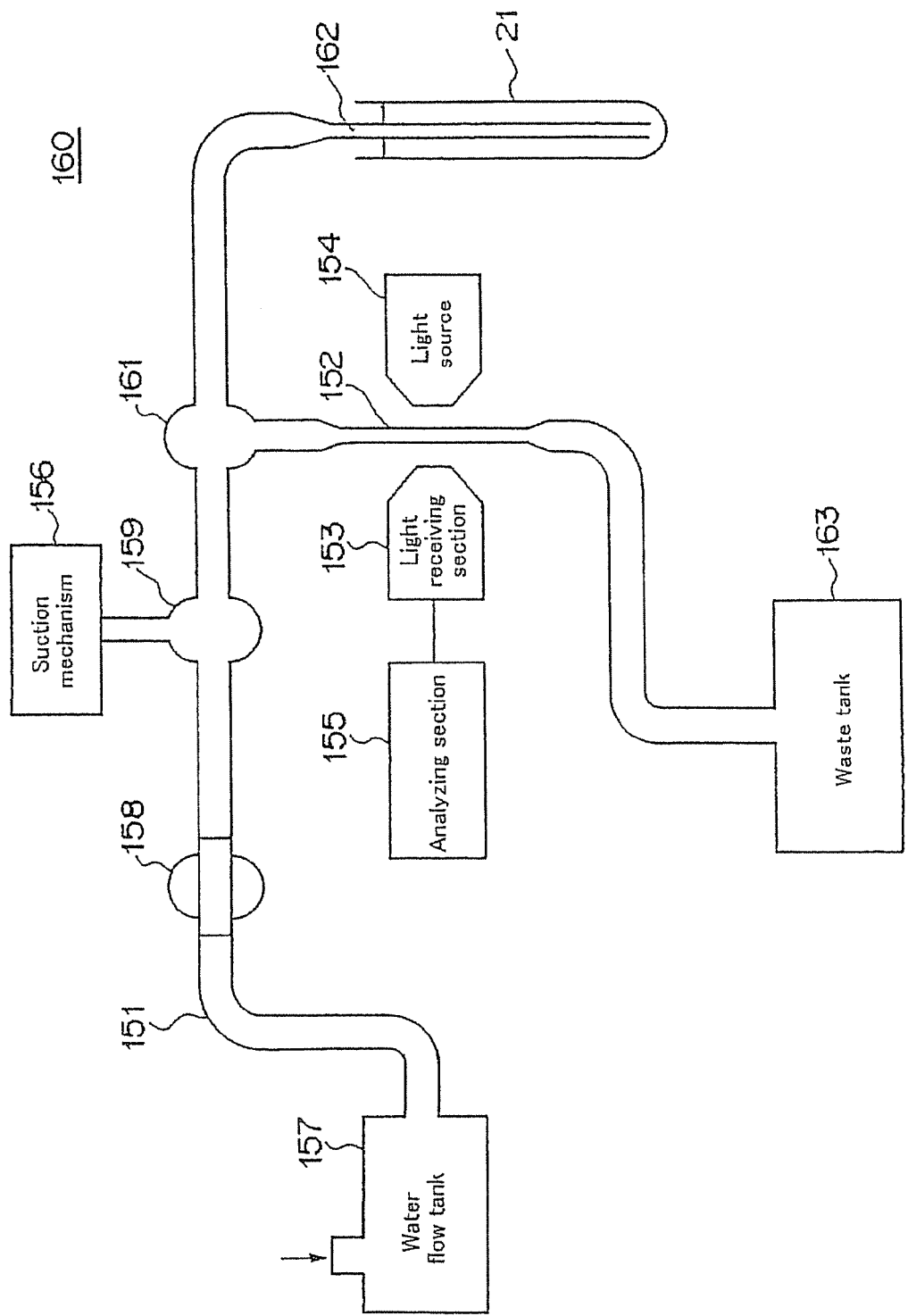
FIG. 18 is a diagram showing a flow cytometer according to a conventional example.

FIG. 17 shows an example of measurement results for the target small objects from the identifying section 32 according to the first embodiment.

FIG. 17 explains as an example, the case of identifying the target small objects shown in FIG. 5.

For example, these flow through the passage in order of; first the small object 34a of a small diameter of FIG. 5 (*a*), second the small object 34b of an intermediate diameter of FIG. 5 (*a*), third the small object 34c of a large diameter of FIG. 5 (*a*), fourth the small object 34e of FIG. 5 (*b*), fifth the small object 34f of FIG. 5 (*c*), sixth the small object 34g of FIG. 5 (*d*), and seventh the small object 34h of FIG. 5 (*e*). Furthermore, this shows an example for the case where these are captured by the measuring section by relatively moving these.

For example, with the first small object, only the square of the shape column is just one third hatched. Therefore, according to the strength, the situation where there is a particle with the smallest diameter of the three kinds, and a labeling substance is not bonded is identified. With the second small object, only the square of the shape column is just two thirds hatched. Therefore, according to the strength, the situation where there is the particle with the central diameter of the three kinds, and a labeling substance is not bonded is identified. With the third small object, only the square of the shape column is completely hatched. Therefore, according to the strength, the situation where there is the particle with the largest diameter of the three kinds, is identified.

With the fourth small object, the square of the shape column is just two thirds hatched, and in the square 45° adjacent thereto, the respective columns for $A_1$, $A_2$ and $A_3$ have the same strength. Therefore the situation where there is the small object having the intermediate diameter, and the molar ratios of the fluorescent substances $A_1$, $A_2$ and $A_3$ serving as the label elements are the same, is identified.

Similarly, with the seventh small object, the situation of labeling where the square of the shape column is completely hatched, and in the square of the A column, the molar ratios of $A_1:A_2:A_3$ are 1:2:1, in the square of the B column, the ratios of $B_1:B_2:B_3$ are 1:1:2, and the ratios of $C_1:C_2:C_3$ have molar ratios 2:1:1, is identified. Regarding the strength of the wavelength of light for the respective columns of FIG. 14, this is appropriately standardized since the molar ratio of the strength for each of the small objects can be measured.

The respective embodiments described above have been specifically described in order to better understand the present invention, however these do not limit other forms. Consequently, these may be modified within a scope which does not alter the gist of the invention. Furthermore, the aforementioned respective constituent elements, components, devices etc, for example the passages, the measuring passages, the measurement points, the optical measuring units, the light receiving fibers, the illumination points, the illumination fibers, the label elements and so on, may be optionally combined with suitable modification. Moreover, in the above description, only the case where light is used as electromagnetic waves has been described. However other wavelength ranges of electromagnetic waves other than visible light such as infrared rays, ultraviolet rays, X-rays, radio waves and the like may be used. Furthermore, measurement by electric field measurement is also possible. Moreover, the description has only been for when a fluorescent substance is used as the label element. However this may be another luminescent material, for example a luminescent material where excitation light is not necessary.

Furthermore, the measurement points and the positional relationship of the illumination points may be variously combined. Moreover, in the aforementioned embodiments, the description has been only for the case where it is necessary to shine light of for example excitation light. However this is not necessarily limited to cases where it is necessary to shine light.

Furthermore, the size of the small objects, the kind of the label elements, the position and the number of the measurement points and the illumination points, the position and size of the passages, the mechanisms, the size of the fibers and so on, is not limited to the aforementioned examples. Moreover, it is also possible to provide for the fibers, optical systems of various types such as filters, branching paths, connectors, lenses and the like.

Furthermore, regarding the magnetic device, the example was described using only the case of measuring by moving the measurement points in a condition with the magnetic small objects accumulated in a static condition in the measurement passage. However the invention is not limited to this example, and for example it is also possible to use the case where when a liquid containing the magnetic small objects is passed through inside the passage, the magnetic small objects are decelerated inside the measurement passage, and are lined up, or the transit time within the measurement passage is prolonged.

In the aforementioned embodiments, only the case of a small diameter passage as the dispersion region section was described, however a flat shape passage or a container is also possible.

Furthermore, in the aforementioned description, only the case of a finite time difference as the temporal relationship between the measurement points was described, however this time difference may be zero. For example, sets of eight measurement points (which may be illumination points) arranged so as to surround the small diameter passage may be arranged along the passage, for example with ten sets in a row, and in each set, eight optical fibers for performing illumination and measurement of a single small object may be radially provided, and measurement performed so that the time difference becomes zero, and measurement performed between the respective sets so that the time difference becomes relatively finite. In this case, a single optical fiber is a light receiving fiber and an illumination fiber.

Moreover, in the aforementioned description, for the measurement points of the measurement device, and for the dispersion region section and the vicinity of the outside of the dispersion region section corresponding to the measurement points, preferably for the measurement unit, the shapes and the spatial distributions of for example; the light receiving section, the attachment jig, the light receiving fibers, the illumination fibers, the illumination side holding section, the light receiving side holding section, the optical fiber connectors and the like, are approximately the same as each other. As a result, measurement deviation can be kept to a minimum.

What is claimed is:

1. A small object identifying method for analyzing target substances or materials comprising:
    a dispersion step comprising dispersing a large quantity of several kinds of small objects having said target substances or materials labeled by a combination of the presence/absence or measure of label elements of several kinds so as to identify each said target substance or material;
    a measuring step comprising distributing and associating kinds of said label elements to two or more measurement points, and measuring the presence/absence or the measure of said label elements of the kinds which have been associated with respective measurement points, for the dispersed said small objects, at respective measurement points having a relative temporal relationship between measurement points; and
    an identifying step comprising associating the measurement results measured at each measurement point, based on said temporal relationship and a positional relationship between said measurement points, to thereby identify said small objects,
    wherein said dispersion step comprises an introducing step which disperses a large quantity of said several kinds of small objects by introducing a liquid for suspending the large quantity of said several kinds of small objects to inside a predetermined dispersion region section, and
    wherein in said measuring step, a velocity along a predetermined movement direction is imparted to said small objects or to two or more measurement points arranged along said movement direction and from which measurements are taken to thereby measure by making said temporal relationship relative between each of the measurement points,
    wherein in said measuring step, the light from inside the dispersion region section is received by a plurality of light receiving fibers with one or more tip portions provided at the measurement points along the predetermined movement direction.

2. A small object identifying method according to claim 1, wherein in said measuring step, said two or more measurement points are arranged in one row or a plurality of rows along said predetermined movement direction, and the arrangement direction of each row is parallel with said predetermined movement direction, and the respective measurement directions from the measurement points belonging to the same row are parallel with each other.

3. A small object identifying method according to claim 1, wherein said dispersion step involves surrounding a liquid containing said small objects with a liquid which does not contain small objects.

4. A small object identifying method according to claim 1, wherein in said measuring step, said label elements of several kinds comprise label elements based on electromagnetic waves of wavelengths of mutually different ranges, and the measure of the label elements based on said electromagnetic waves is the strength of the electromagnetic waves, and said several kinds of labeled small objects are mutually identified by differences in combinations of wavelength ranges of said electromagnetic waves of the label elements on the small objects, or combinations of the wavelength range and intensity ratio thereof.

5. A small object identifying method according to claim 1, wherein said small objects comprise a reference small object having a label, and a target small object, and
    wherein said dispersion step disperses as said small objects, a reference small object having a label which becomes a distinct reference, together with said target small object, and said identifying step incorporates the measurement results for said reference small object, to thereby identify the kind of said target small object.

6. A small object identifying method according to claim 1, wherein said small objects each comprise a magnetic particle, and
    wherein in said measuring step, measurement is performed by remotely controlling said dispersed small objects by applying or removing a magnetic field to or from said small objects.

7. A small object identifying device comprising:
    a dispersion region section comprising means for dispersing a large quantity of several kinds of small objects which are labeled by a combination of the presence/absence or measure of label elements of several kinds;
    a measuring device comprising means for distributing and associating kinds of said label elements to two or more measurement points, and means for measuring the presence/absence or measure of said label elements of the kinds which have been associated with respective measurement points, for said small objects which are dispersed inside said dispersion region section, at respective measurement points having a relative temporal relationship between measurement points; and
    an identifying section comprising means for associating the measurement results measured at each measurement point, based on said temporal relationship and a positional relationship between said measurement points, to thereby identify said small objects;

wherein the measurement points from which measurements are taken using said measurement device are arranged along a predetermined movement direction and there is provided a moving section which imparts a predetermined velocity along said predetermined movement direction to said measurement points or to said small objects, wherein the measuring device is an optical measuring unit, and the optical measuring unit has a plurality of light receiving fibers which receive light from inside a dispersion region section with one or two or more tip portions provided at a plurality of measurement points along the predetermined movement direction, and an attachment jig which fixedly attaches the tip portions to said measurement points.

8. A small object identifying device according to claim 7, wherein said two or more measurement points of said measurement device are arranged in one row or a plurality of rows along said predetermined movement direction, and the arrangement direction of each row is parallel with said predetermined movement direction, and the respective measurement directions from the measurement points belonging to the same row are parallel with each other.

9. A small object identifying device according to claim 7, wherein within said dispersion region, a liquid containing said small objects is surrounded with a liquid which does not contain small objects.

10. A small object identifying device according to claim 7, wherein said label elements are labeled so as to be mutually identifiable by differences in at least one of:

combinations of wavelength range of electromagnetic waves used in labeling said label elements, and combinations of their wavelength range and intensity ratio, and wherein said measuring device comprises:

a plurality of wave receiving sections which receive electromagnetic waves at several of said measurement points, an attachment jig which fixedly attaches the tips of said wave receiving section to said measurement points, and a measuring section which measures the intensity of the received electromagnetic waves for each of the wave receiving sections.

11. A small object identifying device according to claim 7, wherein said small objects comprise a reference small object having a label, and a target small object, and wherein said identifying section, in the case where the reference small object having the label which becomes a distinct reference is dispersed together with said target small object, incorporates the measurement result for said reference small object, to thereby identify the kind of said target small object.

12. A small object identifying device according to claim 7, wherein said optical measuring unit comprises:

a plurality of illumination fibers with one or two or more tip portions provided at illumination points corresponding to said two or more measurement points, and wherein said attachment jig attaches said light receiving fibers and illumination fibers to said diffusion region section so that direction of the optical axes of the tip portions of the illumination fibers provided at the illumination points and the tip portions of the light receiving fibers provided at said measurement points are either axially aligned or intersect at a predetermined angle within said dispersion region section.

13. A small object identifying device according to claim 12, wherein said attachment jig comprises:

an illumination side holding section which holds the tip portions of the plurality of illumination fibers in an array such that their tip faces are positioned on an end face of the illumination side holding section or pass through the end face, a light receiving side holding section which holds the tip portions of the plurality of light receiving fibers in an array such that their tip faces are positioned on an end face of the light receiving side holding section or pass through the end face, and a dispersion region section is formed between the two end faces of said illumination side holding section and said light receiving side holding section, said dispersion region section comprising a long thin slit shape hole provided in a thin plate which is sandwiched from the front and rear by the two end faces of said illumination side holding section and said light receiving side holding section.

14. A small object identifying device according to claim 7, further comprising a magnetic force device which can remotely control said small objects by applying or removing a magnetic field to or from the inside of said region section.

15. A small object identifying device according to claim 7, wherein said measuring device is an optical measuring unit, and said optical measuring unit comprises:

an illumination section which shines excitation light which excites said luminescent material in the illumination points corresponding to two or more of said measurement points.

16. A small object identifying device according to claim 12, wherein said measuring device is an optical measuring unit, the optical measuring unit comprising:

a light receiving section having a plurality of light receiving fibers with one or two or more tip portions provided on a plurality of measurement points along a predetermined movement direction, which receive light from inside the dispersion region section, and a plurality of illumination fibers with one or two or more tip portions provided at illumination points corresponding to two or more of said measurement points, wherein the core diameter of the tip portions of said light receiving fibers is smaller than the core diameter of said illumination fibers.

17. A small object identifying method according to claim 2, wherein said dispersion step involves surrounding a liquid containing said small objects with a liquid which does not contain small objects.

* * * * *